United States Patent
Wahlstrand et al.

(10) Patent No.: US 7,317,947 B2
(45) Date of Patent: Jan. 8, 2008

(54) HEADSET RECHARGER FOR CRANIALLY IMPLANTABLE MEDICAL DEVICES

(75) Inventors: Carl D. Wahlstrand, Lino Lakes, MN (US); William C. Phillips, Brooklyn Park, MN (US); Robert M. Skime, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 50 days.

(21) Appl. No.: 10/835,548

(22) Filed: Apr. 29, 2004

(65) Prior Publication Data

US 2005/0004619 A1 Jan. 6, 2005

Related U.S. Application Data

(60) Provisional application No. 60/471,262, filed on May 16, 2003.

(51) Int. Cl.
*A61N 1/378* (2006.01)
(52) U.S. Cl. .......................................... 607/61; 607/60
(58) Field of Classification Search ................ 607/46, 607/55–57, 60, 61, 103, 139, 149, 154–156, 607/136, 137; 600/33, 379
See application file for complete search history.

(56) References Cited

U.S. PATENT DOCUMENTS

| | | | |
|---|---|---|---|
| 3,310,051 | A | 3/1967 | Schulte |
| 3,447,160 | A * | 6/1969 | Teder ............................ 2/209 |
| 3,522,811 | A | 8/1970 | Schwartz et al. |
| 3,690,325 | A | 9/1972 | Kenny |
| 3,724,467 | A | 4/1973 | Avery et al. |

(Continued)

FOREIGN PATENT DOCUMENTS

DE  3940632  12/1990

(Continued)

OTHER PUBLICATIONS

Notification of Transmittal of the International Search Report and the Written Opinion of the International Searching Authority, International Application No. PCT/US2004/015084, filed May 12, 2004.

(Continued)

*Primary Examiner*—George R. Evanisko
*Assistant Examiner*—Michael Kahelin
(74) *Attorney, Agent, or Firm*—Shumaker & Sieffert, P.A.

(57) ABSTRACT

The invention is directed to a recharging system and associated techniques to recharge an implantable medical device (IMD). In particular, a recharging system according to the invention comprises a headset having an energy delivery module that delivers energy to a power source of an IMD implanted on or within the cranium of a patient. The energy delivery module may comprise a coil for inductive transfer of energy to the power source. The headset may be configured for placement over the head of the patient, and may further only partially cover the top of the head. The energy delivery module may be adjustably coupled to the headset. In some embodiments, the position of the energy delivery module may be adjusted along three or four axes, including a rotational axis, allowing the coil to be placed over an IMD located at any of a variety of locations on or within the cranium.

31 Claims, 11 Drawing Sheets

U.S. PATENT DOCUMENTS

| | | | |
|---|---|---|---|
| 3,913,587 A | 10/1975 | Newash | |
| 4,013,081 A | 3/1977 | Kolenik | |
| 4,040,412 A | 8/1977 | Sato | |
| 4,266,552 A | 5/1981 | Dutcher et al. | |
| 4,328,813 A | 5/1982 | Ray | |
| 4,399,819 A | 8/1983 | Cowdery | |
| 4,399,820 A | 8/1983 | Wirtzfeld et al. | |
| 4,616,655 A | 10/1986 | Weinberg et al. | |
| 4,911,178 A | 3/1990 | Neal | |
| 4,928,696 A * | 5/1990 | Henderson et al. | 600/383 |
| 4,969,899 A | 11/1990 | Cox, Jr. | |
| 5,085,644 A | 2/1992 | Watson et al. | |
| 5,197,332 A * | 3/1993 | Shennib | 73/585 |
| 5,220,929 A | 6/1993 | Marquit | |
| 5,271,397 A | 12/1993 | Seligman et al. | |
| 5,314,451 A | 5/1994 | Mulier | |
| 5,314,453 A * | 5/1994 | Jeutter | 607/61 |
| 5,411,537 A | 5/1995 | Munshi et al. | |
| 5,411,538 A | 5/1995 | Lin | |
| H1465 H | 7/1995 | Stokes | |
| 5,455,999 A | 10/1995 | Owens et al. | |
| 5,477,855 A | 12/1995 | Schindler et al. | |
| 5,489,225 A | 2/1996 | Julian | |
| 5,554,194 A | 9/1996 | Sanders | |
| 5,571,148 A | 11/1996 | Loeb et al. | |
| 5,573,551 A | 11/1996 | Lin et al. | |
| 5,638,832 A | 6/1997 | Singer et al. | |
| 5,645,586 A | 7/1997 | Meltzer | |
| 5,678,559 A * | 10/1997 | Drakulic | 600/544 |
| 5,702,430 A | 12/1997 | Slimon et al. | |
| 5,741,313 A | 4/1998 | Nason et al. | |
| 5,755,743 A | 5/1998 | Volz et al. | |
| 5,776,169 A | 7/1998 | Schroeppel | |
| 5,792,067 A | 8/1998 | Karell | |
| 5,800,535 A | 9/1998 | Howard, III | |
| 5,814,095 A | 9/1998 | Leysieffer et al. | |
| 5,836,935 A | 11/1998 | Ashton et al. | |
| 5,843,150 A | 12/1998 | Adams et al. | |
| RE36,120 E | 3/1999 | Karell | |
| 5,895,414 A | 4/1999 | Sanchez-Zambrano | |
| 5,896,647 A | 4/1999 | Shkuratoff | |
| 5,919,215 A | 7/1999 | Haeg et al. | |
| 5,935,154 A | 8/1999 | Westlund | |
| 5,941,905 A | 8/1999 | Single | |
| 5,941,906 A | 8/1999 | Barreras, Sr. et al. | |
| 5,984,859 A | 11/1999 | Lesinski | |
| 5,991,664 A | 11/1999 | Seligman | |
| 6,006,124 A | 12/1999 | Fischell et al. | |
| 6,016,449 A | 1/2000 | Fischell et al. | |
| 6,016,593 A | 1/2000 | Kyrstein | |
| 6,061,593 A | 5/2000 | Fischell et al. | |
| 6,067,474 A | 5/2000 | Schulman et al. | |
| 6,128,538 A | 10/2000 | Fischell et al. | |
| 6,131,581 A | 10/2000 | Leysieffer et al. | |
| 6,134,474 A | 10/2000 | Fischell et al. | |
| 6,154,677 A | 11/2000 | Leysieffer | |
| 6,168,580 B1 | 1/2001 | Yardley | |
| 6,176,879 B1 | 1/2001 | Leysieffer et al. | |
| 6,214,032 B1 | 4/2001 | Loeb et al. | |
| 6,230,049 B1 | 5/2001 | Fischell et al. | |
| 6,248,080 B1 | 6/2001 | Miesel et al. | |
| 6,248,126 B1 | 6/2001 | Lesser et al. | |
| 6,259,951 B1 | 7/2001 | Kuzma et al. | |
| 6,266,556 B1 | 7/2001 | Ives et al. | |
| 6,269,266 B1 | 7/2001 | Leysieffer | |
| 6,272,382 B1 | 8/2001 | Lenarz et al. | |
| 6,308,101 B1 | 10/2001 | Gord et al. | |
| 6,324,428 B1 | 11/2001 | Weinberg et al. | |
| 6,324,433 B1 | 11/2001 | Errico | |
| 6,330,468 B1 | 12/2001 | Scharf | |
| 6,354,299 B1 | 3/2002 | Fischell et al. | |
| 6,356,792 B1 | 3/2002 | Errico et al. | |
| 6,358,281 B1 * | 3/2002 | Berrang et al. | 623/10 |
| 6,360,122 B1 | 3/2002 | Fischell et al. | |
| 6,366,813 B1 | 4/2002 | DiLorenzo | |
| 6,415,184 B1 | 7/2002 | Ishikawa et al. | |
| 6,427,086 B1 | 7/2002 | Upton et al. | |
| 6,480,743 B1 | 11/2002 | Kirkpatrick et al. | |
| 6,490,486 B1 | 12/2002 | Bradley | |
| 6,505,077 B1 | 1/2003 | Kast et al. | |
| 6,516,227 B1 | 2/2003 | Meadows et al. | |
| 6,516,808 B2 | 2/2003 | Schulman | |
| 6,537,200 B2 | 3/2003 | Leysieffer et al. | |
| 6,554,762 B2 | 4/2003 | Leysieffer | |
| 6,560,486 B1 | 5/2003 | Frei et al. | |
| 6,565,503 B2 | 5/2003 | Leysieffer et al. | |
| 6,567,703 B1 | 5/2003 | Thompson et al. | |
| 6,575,894 B2 | 6/2003 | Leysieffer et al. | |
| 6,597,954 B1 | 7/2003 | Pless et al. | |
| 6,618,623 B1 | 9/2003 | Pless et al. | |
| 6,626,680 B2 | 9/2003 | Ciurzynski et al. | |
| 6,648,914 B2 | 11/2003 | Berrang et al. | |
| 6,671,544 B2 | 12/2003 | Baudino | |
| 6,726,678 B1 | 4/2004 | Nelson et al. | |
| 6,736,770 B2 | 5/2004 | Leysieffer et al. | |
| 6,805,998 B2 | 10/2004 | Jenson et al. | |
| 7,103,415 B2 | 9/2006 | Probst et al. | |
| 2001/0033953 A1 | 10/2001 | Takeuchi et al. | |
| 2001/0051819 A1 | 12/2001 | Fischell et al. | |
| 2002/0002390 A1 | 1/2002 | Upton et al. | |
| 2002/0013612 A1 | 1/2002 | Whitehurst | |
| 2002/0019669 A1 | 2/2002 | Berrang et al. | |
| 2002/0051550 A1 | 5/2002 | Leysieffer | |
| 2002/0072770 A1 | 6/2002 | Pless | |
| 2002/0077670 A1 | 6/2002 | Archer et al. | |
| 2002/0099412 A1 | 7/2002 | Fischell et al. | |
| 2002/0103510 A1 | 8/2002 | Bardy et al. | |
| 2002/0161403 A1 | 10/2002 | Meadows et al. | |
| 2002/0165588 A1 | 11/2002 | Fraley et al. | |
| 2002/0169485 A1 | 11/2002 | Pless et al. | |
| 2002/0177882 A1 | 11/2002 | DiLorenzo | |
| 2003/0004428 A1 | 1/2003 | Pless et al. | |
| 2003/0004546 A1 | 1/2003 | Casey | |
| 2003/0040781 A1 | 2/2003 | Sunderland et al. | |
| 2003/0073972 A1 | 4/2003 | Rosenman et al. | |
| 2003/0085684 A1 | 5/2003 | Tsukamoto et al. | |
| 2003/0088294 A1 | 5/2003 | Gesotti | |
| 2003/0109903 A1 | 6/2003 | Berrang et al. | |
| 2003/0130706 A1 * | 7/2003 | Sheffield et al. | 607/46 |
| 2003/0171787 A1 | 9/2003 | Money et al. | |
| 2004/0176750 A1 | 9/2004 | Nelson et al. | |

FOREIGN PATENT DOCUMENTS

| | | |
|---|---|---|
| EP | 1 145 735 A2 | 10/2001 |
| EP | 1 145 736 A2 | 10/2001 |
| GB | 1 161 579 | 8/1969 |
| WO | WO 92/020402 | 11/1992 |
| WO | WO 99/06108 | 2/1999 |
| WO | WO 99/34758 | 7/1999 |
| WO | WO 00/13743 | 3/2000 |
| WO | WO 00/040295 | 7/2000 |
| WO | WO 01/10369 | 2/2001 |
| WO | WO 01/28622 | 4/2001 |
| WO | WO 01/039830 | 6/2001 |
| WO | WO 01/060450 | 8/2001 |
| WO | WO 01/97906 | 12/2001 |
| WO | WO 02/005590 | 1/2002 |
| WO | WO 02/056637 | 7/2002 |
| WO | WO 02/083207 | 10/2002 |
| WO | WO 02/083208 | 10/2002 |
| WO | WO 02/083233 | 10/2002 |
| WO | WO 03/026739 | 4/2003 |
| WO | WO 03/076012 | 9/2003 |

| | | |
|---|---|---|
| WO | WO 04/043536 | 5/2004 |

OTHER PUBLICATIONS

U.S. Appl. No. 10/731,699, filed Dec. 9, 2003, entitled "Coupling Module Of A Modular Implantable Medical Device,".

U.S. Appl. No. 10/731,868, filed Dec. 9, 2003, entitled "Implantation of Low-Profile Implantable Medical Device."

U.S. Appl. No. 10/730,873, filed Dec. 9, 2003, entitled "Overmold for a Modular Implantable Medical Device."

U.S. Appl. No. 10/731,881, filed Dec. 9, 2003, entitled "Reducing Relative Intermodule Motion in a Modular Implantable Medical Device."

U.S. Appl. No. 10/730,878, filed Dec. 9, 2003, entitled "Lead Connection Module of a Modular Implantable Medical Device."

U.S. Appl. No. 10/730,877, filed Dec. 9, 2003, entitled "Low-Profile Implantable Medical Device."

U.S. Appl. No. 10/731,867, filed Dec. 9, 2003, entitled "Concavity of an Implantable Medical Device."

U.S. Appl. No. 10/731,638, filed Dec. 9, 2003, entitled "Modular Implantable Medical Device."

U.S. Appl. No. 10/731,869, filed Dec. 9, 2003, entitled "Modular Implantable Medical Device."

U.S. Appl. No. 10/835,527, filed Apr. 29, 2004, entitled "Implantation of Implantable Medical Device".

U.S. Appl. No. 10/835,232, filed Apr. 29, 2004, entitled "Explanation of Implantable Medical Device."

U.S. Appl. No. 10/835,233, filed Apr. 29, 2004, entitled "Implantable Medical Device With A Nonhermetic Battery."

U.S. Appl. No. 10/835,245, filed Apr. 29, 2004, entitled "Battery Housing Configuration."

Notification of Transmittal of the International Preliminary Report on Patentability for PCT/US2004/015084, dated Jun. 27, 2005 (5 pgs.).

* cited by examiner

HEADSET RECHARGER FOR CRANIALLY IMPLANTABLE MEDICAL DEVICES

This application claims the benefit of U.S. provisional application Ser. No. 60/471,262, filed May 16, 2003, the entire content of which is incorporated herein by reference.

TECHNICAL FIELD

The invention relates to medical devices, and more particularly, to techniques for recharging power sources of implantable medical devices.

BACKGROUND

Depending on the application for which they are implanted in a patient, implantable medical devices (IMDs) may include a variety of electrical and/or mechanical components. Typically, an IMD includes a rigid housing that houses all of its components, which are generally fragile, to protect the components from forces to which they would otherwise be exposed when implanted within the human body. In order to avoid potentially harmful interactions between the components and bodily fluids, e.g., corrosion, IMD housings are typically hermetically sealed. Many IMD housings are fabricated from Titanium because of its desirable rigidity and biocompatibility. Components common to most IMDs include a hybrid circuit that includes digital circuits, e.g., integrated circuit chips and/or a microprocessor, and analog circuit components. Most IMDs also include a battery to provide power to the digital and analog circuit components.

Most IMDs rely on a non-rechargeable, e.g., primary, battery as a source of power. When a primary battery is no longer able to provide adequate power for an IMD, the IMD must be explanted, and either the battery or the entire IMD must be replaced. The "lifetime" of a primary battery depends on the power requirements of the IMD, and the amount of power stored by the battery. The amount of power stored by a battery is closely related to its size, while the amount of power required by an IMD is primarily dependent of the type of therapy delivered by the IMD. For example, implantable neurostimulators and implantable pumps consume power at a relatively higher rate than cardiac pacemakers and IMDs used primarily for patient monitoring. Consequently, designers of IMDs with high power requirements, such as implantable neurostimulators and implantable pumps, often must choose between use of an undesirably large primary battery, or potentially exposing the patient to the risks associated with an eventual surgical procedure to explant the current IMD and implant a new IMD.

In response to the problems associated with the use of primary batteries, some IMDs with high power consumption have been configured as "radio frequency" (RF) systems in which the IMD does not include an implanted power source, but instead receives power from an external power source via transcutaneous inductive energy transfer. Typically the external power source includes a rechargeable battery and is coupled to a primary (external) coil, and the IMD includes or is coupled to a secondary (implanted) coil. Because the IMD in such systems does not include an internal power source, the patient must always wear, or otherwise carry, the external power source, and must keep the primary coil proximate to and aligned with the secondary coil at all times. Further, the patient may periodically have their movement restricted while the external power source is recharged, e.g., via a wall receptacle. On the whole, patients may view such systems as burdensome and restricting.

Other IMDs have been configured to include a rechargeable power source, e.g., a rechargeable battery, within the IMD. Typically, the rechargeable power source is periodically recharged by an external power source, i.e., a recharging device, via transcutaneous inductive energy transfer. Rechargeable batteries used in IMDs may have a longer lifetime and/or a smaller size than primary batteries. Further, when an IMD uses a rechargeable battery, the patient is free to move without the recharging device between recharging sessions.

The effectiveness of the recharging sessions, e.g., the time required to recharge the rechargeable battery, is dependant upon a number of considerations, such as the amplitude and frequency of the current induced in the secondary coil. The amplitude of the current induced in the secondary coil is, in turn, dependent of the proximity and alignment of the primary and secondary coils. Conventional IMD recharging devices may make it difficult for the patient to properly align the primary coil with the secondary coil, and/or to maintain proper alignment during a recharging session. Patients may have particular difficulty achieving and maintaining proper alignment for recharging where their IMD is implanted on or within their cranium. In particular, patients may have difficulty properly aligning the coils on a part of the body which they can see, if at all, only with the aid of a mirror. Further, traditional means for maintaining alignment of the coils during a recharge session, e.g., an adhesive patch carrying the primary coil, may be ineffective in cases in which the IMD is located beneath the patient's hair.

SUMMARY

In general, the invention is directed to a recharging system and associated techniques to recharge a power source of an implantable medical device (IMD) that is implanted on or within a cranium of a patient. In particular, the recharging system comprises a headset having an energy delivery module coupled to the headset. In some embodiments, the energy delivery module comprises a primary coil that delivers energy to the power source of the IMD via transcutaneous inductive energy transfer to a secondary coil associated with the IMD. The headset may be configured for placement over the head of the patient, may only partially cover the top of the patient's head, and the size of the headset may be adjusted in the manner traditionally associated with audio headphones.

The energy delivery module may be adjustably coupled to the headset to allow alignment with a recharge module, e.g., a secondary coil, associated with the IMD. The recharge module may be located within the IMD, substantially co-located with the IMD, or may be located some distance from the IMD. In some embodiments, the energy delivery module is coupled to the headset by a coupling member, which is adjustably coupled to the headset to allow the position of the energy delivery module to be adjusted. In exemplary embodiments, the position of the energy delivery module is adjustable along at least two axes and, in some embodiments, is adjustable along three or four axes including a rotational axis.

The coupling member may include a first end coupled to the headset and a second end coupled to the energy delivery module. The adjustable coupling of the coupling member to the headset may permit lateral, posterior, and anterior movement of the energy delivery module with respect to the head of the patient. The coupling member may further pivot about the point at which it is coupled to the headset to permit rotational motion of the energy delivery module. In some embodiments, the coupling member may be malleable or made malleable, e.g., via the application of heat, and the may be formed, e.g., molded, to the curvature of the patient's head.

The coupling member may be coupled to the headset by a fixation mechanism. The fixation mechanism may be adjusted between a first state in which the position of the energy delivery module may be adjusted, and a second state in which the position of the energy delivery module is substantially fixed. The fixation mechanism may be, for example, a nut and bolt mechanism.

A stabilizing member may also be coupled to and/or extend from the headset to stabilize the position of the headset on the head of the patient. In some embodiments, the position of stabilizing member may be adjusted and fixed via a fixation mechanism as described above with reference to the coupling member. In some embodiments, the stabilizing member may be malleable or made malleable, e.g., via the application of heat, and the may be molded to the curvature of the patient's head.

The recharging system may further include a recharge control unit that controls the delivery of energy to the power source of the IMD. In some embodiments, the recharge control unit includes a rechargeable battery, and controls delivery of energy from the rechargeable battery to the power source of the IMD.

The recharge control unit may also include a telemetry circuit that is coupled to a telemetry antenna, which is in turn coupled to the headset, and the recharge control unit may communicate with the IMD via the telemetry antenna and telemetry circuit. The recharge control module may receive recharge status information from the IMD, such as an indication of the current charge level of the IMD power source or an indication that the IMD power source is fully recharged. In some embodiments in which the energy delivery module comprises a primary coil, the telemetry antenna may comprise the primary coil. In other embodiments, the telemetry antenna may be coupled to the headset by same adjustable coupling member as the energy delivery module, or a different adjustable coupling member than that which couples the energy delivery module to the headset.

The recharge control unit may also include a user interface, and may provide information to the patient via the user interface. For example, the recharge control module may provide alignment information to the patient, such as an indication when the energy delivery module is properly aligned with a recharge module of the IMD. As another example, the recharge control module may provide recharge status information, such as an estimated time remaining for the recharge session, an indication of extent to which the IMD power source is currently charged, or an indication that the power source is fully recharged and the recharge session is complete. The user interface may include a speaker and/or a display, and the recharge control unit may present the information to the patient audibly and/or visually. In some embodiments, the patient may also control initiation and/or termination of energy delivery via the user interface. In some embodiments, the recharge module may store files for patient entertainment, such as MP3 song files, and may play files selected by the patient via the user interface during a recharge session. In some embodiments, the headset may include one or more earpieces that include a speaker, and the recharge control device may audibly present information to the patient and play audio entertainment files via the speakers.

In some embodiments, the recharge control module is housed separately from the headset, and coupled to at least one of the headset and the energy delivery module via a conductor, e.g., a cable. In such embodiments, the recharge control module may be configured to be worn by the patient, e.g., may be configured to be attached to a belt or other clothing of the patient. In other embodiments, the recharge control module may be integrated with the headset. For example, in embodiments in which the headset includes one or more earpieces, the recharge control module may be included within a single earpiece, or the components of the recharge control may be distributed between two earpieces.

The IMD may be, for example, an implantable neurostimulator or implantable pump. In some embodiments, the IMD takes the form of a modular IMD in which components of the IMD, such as control electronics, the power source, and a recharge module, e.g., a secondary coil, are housed within separate modules. Because its components are distributed into a plurality of modules, a modular IMD may have a low profile that provides cosmetic, patient comfort, and clinical acceptability benefits when the modular IMD is implanted on the cranium of the patient beneath the patient's scalp. However, a recharge device according to the invention may be used to recharge any medical device implanted on or within the cranium of a patient.

In one embodiment, a system comprises a headset configured for placement over a head of a patient that partially covers a top of the head, and an energy delivery module coupled to the headset that delivers energy to a power source of a medical device that is implanted at least one of on or within a cranium of the patient.

In another embodiment, a system comprises a headset that is configured for placement over a head of a patient, and an energy delivery module that is adjustably coupled to the headset, and that delivers energy to a power source of a medical device that is implanted at least one of on or within a cranium of the patient.

In another embodiment, a method comprises placing a headset on a head of a patient, adjusting a position of an energy delivery module that is coupled to the headset to locate the energy delivery module proximate to a medical device implanted at least one of on or within a cranium of the patient, and adjusting a fixation mechanism to substantially fix the energy delivery module in a position proximate the medical device.

In another embodiment, a method comprises delivering energy to a power source of a medical device implanted at least one of on or within a cranium of a patient via an energy delivery module coupled to a headset that is proximate to the medical device when the headset is placed on a head of the patient.

In another embodiment, the invention is directed to a system that includes a medical device and a recharging system. The medical device includes a power source, is implanted at least one of on or within a cranium of a patient, is coupled to a lead that is implanted at least one of within or adjacent to a brain of the patient, and at least one of delivers stimulation to the brain or monitors electrical activity within the brain via the lead. The recharging system includes a headset that is configured for placement over a head of the patient, and an energy delivery module that is adjustably coupled to the headset and delivers energy to the power source of the medical device.

In another embodiment, the invention is directed to a system that includes a medical device and a recharging system. The medical device includes a rechargeable battery. The recharging system includes a headset that is configured for placement over a head of the patient, and an energy delivery module that is adjustably coupled to the headset and delivers energy to the power source of the medical device.

The invention may be capable of providing one or more advantages. For example, in embodiments in which a recharging system includes an energy delivery module that is adjustably coupled to the headset, the energy delivery module may be positioned proximate to an IMD, e.g., a recharge module of the IMD, located at any of a variety of positions on or within the cranium of a patient. Further, the position of the energy delivery module may be adjusted to align the energy delivery module with the recharge module, and therefore to provide for efficient recharging of the IMD. In some embodiments, the energy delivery module may be substantially fixed in a desired position, so that proper alignment may be maintained during a recharging session. Further, in some cases, the position of the energy delivery module may be adjusted and fixed once, e.g., by a clinician during a fitting session at a clinic, and recharging system may be used by the patient at home without further adjustment of the position of the energy delivery module for the life of the IMD. By providing adjustability, the recharge system may charge IMDs implanted in a variety of implant locations for treatment or monitoring of a variety of conditions and to further account for the anatomical differences between patients. Moreover, the adjustable recharge system may replace many implant location and patient dependant recharge systems by providing a "one-size-fits-all" recharge approach.

In embodiments of the recharging system in which the headset is coupled to or includes a stabilizing member, the stabilizing member may stabilize the position of the headset on the patient's head. The stabilizing member may facilitate consistent alignment of the energy delivery module with the recharge module of the IMD. In particular, the stabilizing member may allow the headset to be consistently placed at a position on the patient's head, and may prevent movement of the headset on the patient's head during recharging sessions. The stabilizing member may be adjusted and fixed, and/or molded, during a fitting session. Further, the size of the headset, e.g., the length of an arc defined by the headset, may be adjusted and fixed based on the size of the patient's head during a fitting session.

Since the headset may only partially cover the head of the patient, the headset may be more comfortable to wear while charging the IMD. Furthermore, in some embodiments, the recharge control unit is incorporated into the headset, e.g., one or more earpieces of the headset, providing a single recharge device that is hands-free. In other embodiments, the recharge control unit may be a separate device that is electrically coupled to the headset, and may feature a more extensive user interface including a display. In such embodiments, the more extensive user interface may allow the patient to more easily interact with the recharge control unit.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
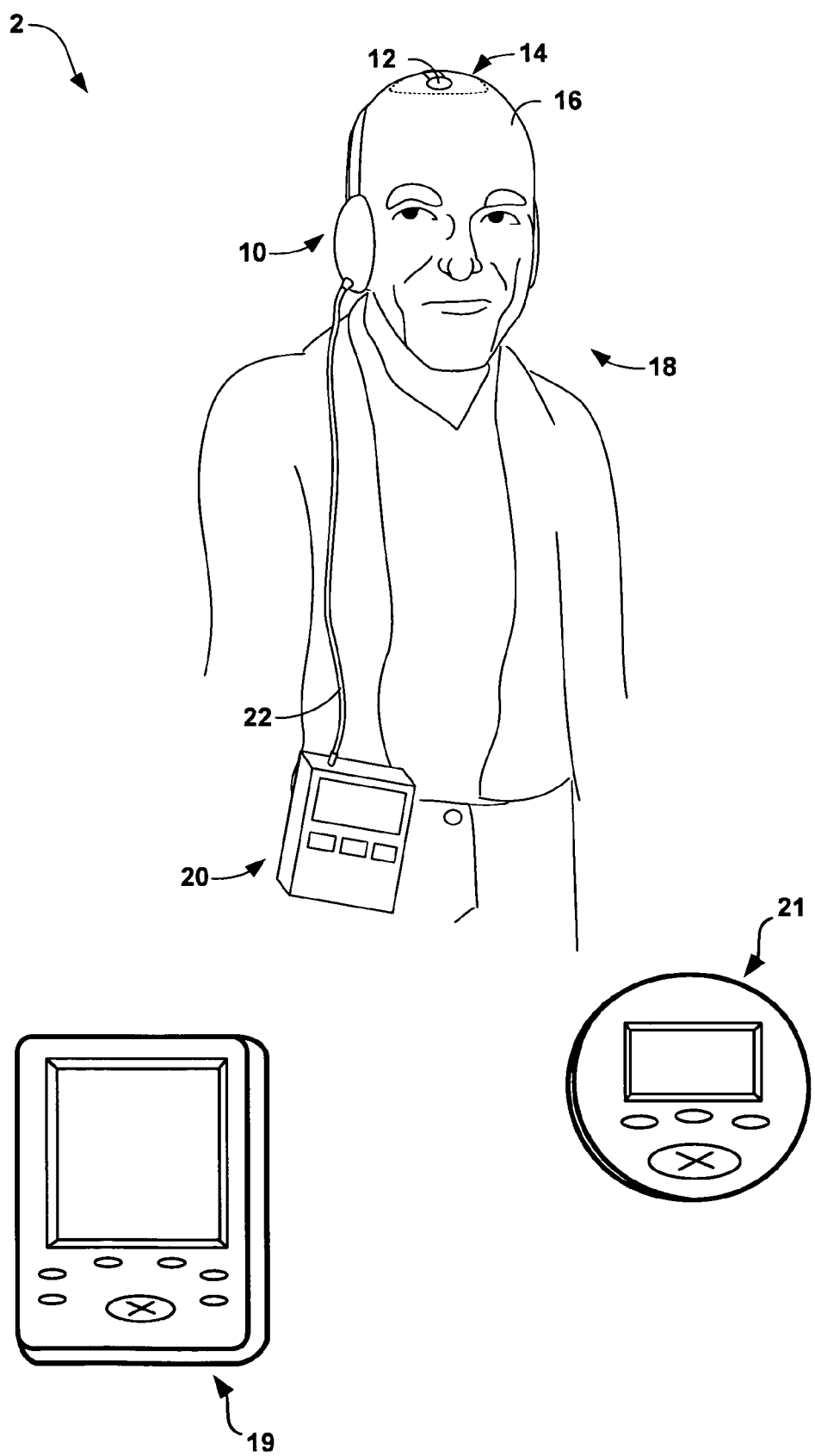
FIG. 1 is a conceptual diagram illustrating an example recharging system that recharges a power source of an implantable medical device (IMD) implanted on the cranium of a patient.

FIG. 1 is a conceptual diagram illustrating an example recharging system 2 that recharges a power source (not shown) of an implantable medical device (IMD) 14 implanted on the cranium of a patient 18. As illustrated in FIG. 1, system 2 includes a headset 10 configured for placement on the head 16 of patient 18, and an energy delivery module 12 coupled to headset 10 that delivers energy to recharge the power source of IMD 14. As will be described in greater detail below, energy delivery module 12 is adjustably coupled to headset 10 such that energy delivery module 12 may be positioned above IMD 14 for efficient delivery of energy to recharge the power source of IMD 14. In exemplary embodiments, energy delivery module 12 comprises a primary coil formed of windings of copper or another highly conductive material that delivers energy to the power source of IMD 14 via transcutaneous inductive energy transfer to a secondary coil associated with IMD 14. The power source of IMD 14 may be, for example, a rechargeable battery or supercapcitor.

As shown in FIG. 1, headset 10 is electrically coupled to a recharge control unit 20 via one or more conductors carried by cable 22. In other embodiments, cable 22 is coupled directly to energy delivery module. Recharge control unit 20 contains circuitry, such as a processor, that controls delivery of energy to the power source of IMD 14 via energy delivery module 12. In some embodiments, the recharge control unit includes a rechargeable battery, and controls delivery of energy from the rechargeable battery to the power source of the IMD via energy delivery module 12.

Recharge control unit 20 may further include a user interface with which patient 18 may interact to activate, monitor and terminate the recharging of IMD 14 as well as other components (not shown), such as a telemetry circuit for communicating with IMD 14 via an antenna that may be, for example, coupled to headset 10 or located within recharge control unit 20. Recharge control unit 20 may receive information relating to the status of the rechargeable power source of IMD 14 from IMD 14 via the telemetry circuit and antenna during recharging, such as an indication of the current charge level of the power source or an indication that the power source is fully recharged. In some embodiments in which energy delivery module 12 comprises a primary coil, the antenna may comprise the primary coil. While shown as a separate from headset 10, the components of recharge control unit 20 may be incorporated into headset 10 by distributing the circuitry, user interface, and other components within earpieces coupled to headset 10 or within a headset bar of headset 10 that supports energy delivery module 12. The headset bar, in these embodiments, may be hollow and store the circuitry in the form of flex tape circuits and capacitors, which may reduce weight and provide for even weight distribution of the components within headset 10.

A clinician or patient 18 may adjust the position of energy delivery module 12 to align energy delivery module 12 with a recharge module, e.g., a secondary coil in embodiments in which energy delivery module 12 comprises a primary coil, associated with IMD 14. The recharge module may be housed within or coupled to IMD 14. The efficiency of the delivery of energy from energy delivery module 12 to the power source of IMD 14 may depend on the degree to which energy delivery module 12 is aligned with the recharge module of IMD 14. Patient 18 or the clinician may also adjust the size of headset 10 to fit the head 16 of patient 12 in the manner traditionally associated with audio headphones, and may adjust and/or mold a stabilizing member (not shown) that extends from headset 10, as will be described in greater detail below. In some embodiments, a clinician may initially make these adjustments to headset 10 and substantially fix headset in a desired configuration during a fitting session at a clinic, and patient 18 may be able to use recharging system 2 at home without further adjustment for substantially the life of IMD 14.

During use, patient 18 places headset 10 upon head 16 to begin recharging the power source of IMD 14. Patient 18 may, via interactions with a user interface of recharge control unit 20, initiate the delivery of energy to the power source of IMD 14 via energy delivery module 12. Recharge control unit 20 may receive information concerning the status of IMD 14, and more particularly, the status of the power source included within IMD 14, via telemetry during recharging. Once the status of the rechargeable battery indicates a full charge, recharge control unit 20 may terminate energy delivery and signal patient 18, e.g., issue a tone or beep, that the recharge is complete, and patient 18 may remove headset 10. In some embodiments, patient 18 may by able to direct recharge control unit 20 to terminate or suspend recharging during a session through interaction with the user interface of recharge control unit 20.

In some embodiments, recharge control unit 20 may communicate with one or more programming devices, such as one or more of a clinician programmer 19 and a patient programmer 21 illustrated in FIG. 1. Clinician programmer 19 and patient programmer 21 may, as shown in FIG. 1, be handheld computing devices. Programmers 19, 21 may include displays, such as a LCD or LED displays, to display information to a user, and may also include keypads, which way be used by a user to interact with the programmers. In some embodiments, the displays may be touch screen displays, and a user may interact with the programmers via their display. A user may also interact with one or both of programmers 19, 21 using a peripheral pointing device, such as a stylus or mouse. A clinician (not shown) may use clinician programmer 19 to program aspects of the delivery of therapy to patient 18 by IMD 14, and patient 18 may use patient programmer 21 to control aspects of the delivery of therapy by IMD 14.

One or both of programmers 19, 21 may communicate with recharge control unit 20 to exchange recharge information with recharge control unit 20. For example, a user, such as a clinician, may use one of programmers 19, 21 to select one or more values used by recharge control unit 20 to control recharging of IMD 14, such as a recharging rate, or a frequency for AC voltage provided to a primary coil in embodiments in which energy delivery module 12 comprises a primary coil. Additionally, the user may use one of programmers 19, 21 to configure a user interface of recharge control unit 20, e.g., to set select the types and formats of indications provided to patient 18 during recharging.

Further, a user, such as a clinician, may use one of programmers 19, 21 to collect recharge information from recharge control unit 20, such as information indicating the duration of one or more recharging session, the quality of alignment between energy delivery module 12 and IMD 14, the rate at which the power source of IMD 14 was recharged, and the status of the power source of IMD 14.

Programmers 19, 21 may communicate with IMD 14, recharge control unit 20, and each other via wireless communication. Programmers 19, 21 may, for example, communicate via wireless communication with IMD 14 using radio frequency (RF) telemetry techniques known in the art. Programmers 19, 21 may communicate with each other and recharge control unit 20 using any of a variety of local wireless communication techniques, such as RF communication according to the 802.11 or Bluetooth specification sets, infrared communication according to the IRDA specification set, or other standard or proprietary telemetry protocols.

Programmers 19, 21 and recharge control unit 20 need not communicate wirelessly, however. For example, programmers 19, 21 and recharge control unit 20 may communicate via a wired connection, such as via a serial communication cable, or via exchange of removable media, such as magnetic or optical disks, or memory cards or sticks. Further, programmers 19, 21 may communication with each other, IMD 14, and recharge control unit 20 via remote telemetry techniques known in the art, communicating via a local area network (LAN), wide area network (WAN), public switched telephone network (PSTN), or cellular telephone network, for example.

Figure 2:
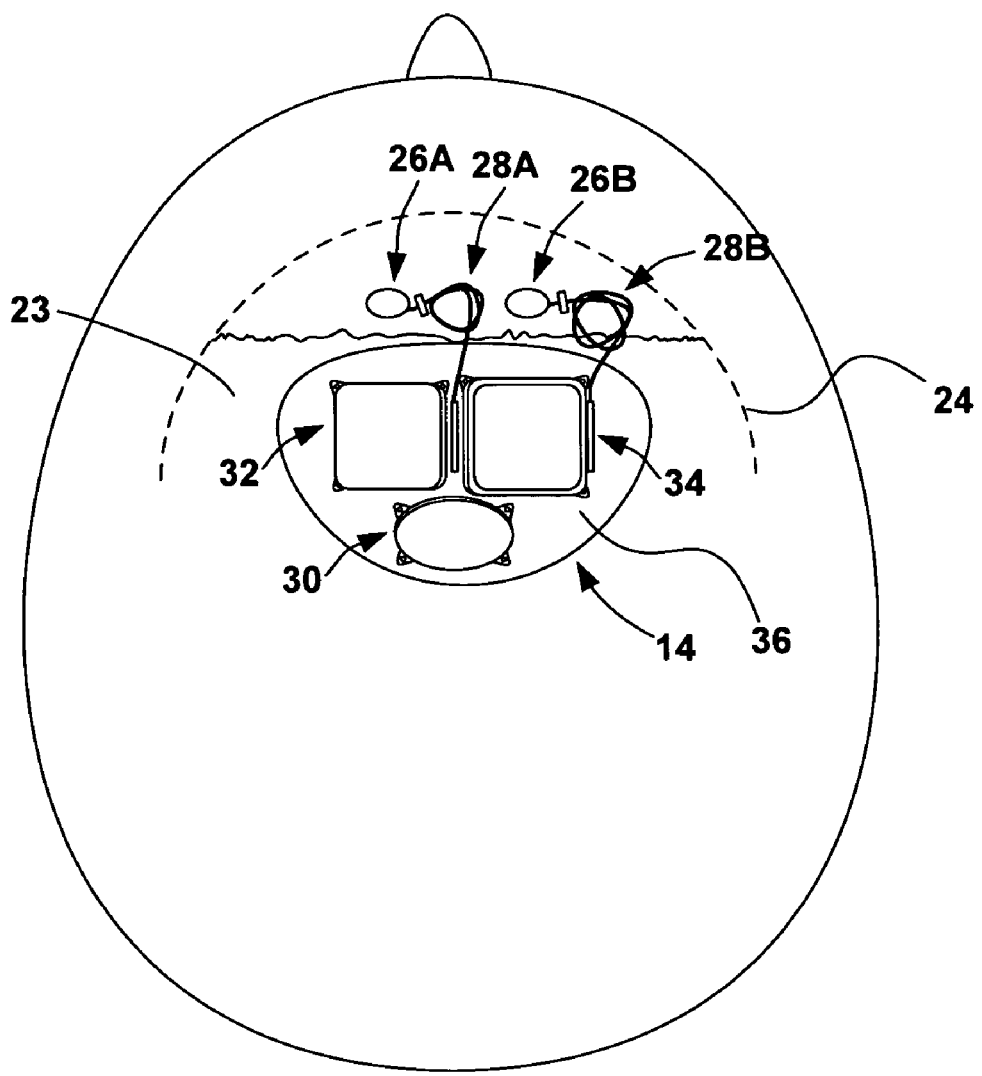
FIG. 2 is a top-view diagram further illustrating the IMD of FIG. 1 implanted on cranium of the patient.

FIG. 2 is a top-view diagram further illustrating IMD 14 implanted on the cranium 23 of patient 18. In order to implant IMD 14 on cranium 23, an incision 24 is made through the scalp of patient 18, and a resulting flap of skin is pulled back to expose the desired area of cranium 23. The incision may, as shown in FIG. 2, be generally shaped like a "C," and such an incision is commonly referred to as a "C-flap" incision.

Holes 26A and 26B (collectively, "holes 26") are drilled through cranium 23, and leads 28A and 28B (collectively, "leads 28") are inserted through holes 26 into the brain of patient 18. Caps may be placed over holes 26 as is known in the art. Leads 28 are connected to IMD 14, either directly or via lead extensions, and IMD 14 may be partially placed within a pocket formed using a hand or tool beneath the scalp behind holes 26.

Once positioned as desired on cranium 23 within the pocket, IMD 14 may be fixed to cranium 16 using attachment mechanisms (not shown), such as bone screws. The skin flap may be closed over IMD 14, and incision 24 may be stapled or sutured. The location on cranium 23 at which IMD 14 is illustrated as implanted in FIG. 2 is merely exemplary, and IMD 14 can be implanted anywhere on the surface of cranium 23.

IMD 14 may deliver stimulation to the brain of patient 18 to, for example, provide deep brain stimulation (DBS)

therapy, or to stimulate the cortex of the brain. Cortical stimulation may involve stimulation of the motor cortex. IMD 14 may be used to treat any nervous system disorder including, but not limited to, epilepsy, pain, psychological disorders including mood and anxiety disorders, movement disorders (MVD), such as, but not limited to, essential tremor, Parkinson's disease, and neurodegenerative disorders. IMD 14 may be employed with leads 28 deployed anywhere in the head or neck including, for example, leads deployed on or near the surface of the skull, leads deployed within the brain, e.g., deep brain leads, or leads deployed beneath the skull and adjacent to the brain, e.g., cortical leads. As other examples, IMD 14 may be employed with leads 28 deployed near or on the dura mater, leads placed adjacent cranial or other nerves in the neck or head, or leads placed directly on the surface of the brain.

IMD 14 is not limited to embodiments that deliver stimulation. For example, in some embodiments IMD 14 may additionally or alternatively monitor one or more physiological parameters and/or the activity of patient 18, and may include sensors for these purposes. Where a therapy is delivered, IMD 14 may operate in an open loop mode (also referred to as non-responsive operation), or in a closed loop mode (also referred to as responsive). IMD 14 may also provide warnings based on the monitoring. Further, in some embodiments modular IMD 14 can additionally or alternatively deliver a therapeutic agent to patient 18, such as a pharmaceutical, biological, or genetic agent. IMD 14 may be coupled to a catheter, and may include a pump to deliver the therapeutic agent via the catheter.

In the embodiment illustrated in FIG. 2, IMD 14 takes the form of a modular IMD that delivers neurostimulation to patient 18. In the illustrated example, IMD 14 includes a recharge module 30, a power module 32, and a control module 34. Recharge module 30 may include, for example, a secondary coil formed of windings of copper or another highly conductive material used to receive energy from a primary coil via transcutaneous inductive energy transfer. For transcutaneous inductive energy transmission, recharge control unit 20 (FIG. 1) may present an alternating current (AC) voltage to a primary coil within energy delivery module 12, which induces an AC voltage on the secondary coil within recharge module 30.

Power module 32 includes the rechargeable power source of IMD 14, e.g., a rechargeable battery. Control module 34 includes control electronics, e.g., a microprocessor, that control the functioning of IMD 14, e.g., control delivery of neurostimulation therapy to patient 18. Each of modules 30, 32, and 34 may include a separate housing to protect the elements therein, and the modules may be coupled by one or more conductors, or the like. In exemplary embodiments, the housings of modules 32 and 34 may be hermetic.

In some embodiments, recharge module 30 is electrically coupled to control module 34, and control module 34 includes electronics to receive energy collected by recharge module 30, and control delivery of the energy to power module 32 in order to recharge the power source therein. For example, in embodiments in which recharge module comprises a secondary coil on which an AC voltage is induced via transcutaneous inductive energy transfer, control module 34 may include a rectifier circuit to convert the AC voltage to a direct current (DC) voltage. In such embodiments, control module 34 provides the DC voltage to the power source of power module 32 to recharge the power source.

The control electronics within control module 34 may also include or be coupled to one or more sensors that sense the status, e.g., voltage or temperature, of the power source within power module 32. The sensors may be located within power module 32 or control module 34. The control electronics may determine the status of the power source based on signals generated by the one or more sensors. Control module 34 may include a telemetry circuit and antenna, and the control electronics may transmit information regarding the status of the power source, e.g., recharge status information, to recharge control unit 20 (FIG. 1) via the telemetry circuit and antenna. The recharge status information may include a voltage, temperature, or information determined on the basis of one or more of the voltage and temperature, such as an estimate of the extent to which the power source is recharged or the time left until the power source is fully recharged.

In the illustrated embodiment, modules 30, 32 and 34 are coupled to a member 36, which may be made of a soft, biocompatible material. Member 36 at least partially encapsulates one or more housings of modules 30, 32, 34, and generally serves to provide a smooth interface between the modules and the body tissue. Member 36 may integrate modules 30, 32 and 34 into a desired form factor, but, where flexible, allow relative intermodule motion. In some embodiments, member 36 incorporates mechanical features to restrict intermodule motion to certain directions or within certain ranges. Member 36 may be made from silicone, and is some embodiments may be made from two or more materials of differing flexibility, such as silicone and a polyurethane. An exemplary polyurethane for this purpose is Tecothane®, which is commercially available from Hermedics Polymer Products, Wilmington, Mass. Member 36 may also be referred to as an "overmold," but use of the term "overmold" herein is not intended to limit the invention to embodiments in which member 36 is a molded structure. Member 36 may be a molded structure, or may be a structure formed by any process.

Although described herein in the context of a modular IMD 14 that delivers neurostimulation therapy, the invention is not so limited. A recharging system according to the invention may be used to recharge a power source of any type of medical device implanted on or within the cranium of a patient, e.g., an implantable neurostimulator, implantable pump, or a medical device used only for patient monitoring or sensing. Further, a recharging system may be used to recharge non-modular IMDs, e.g., IMDs in which the components are located within a single housing.

Figure 3A:
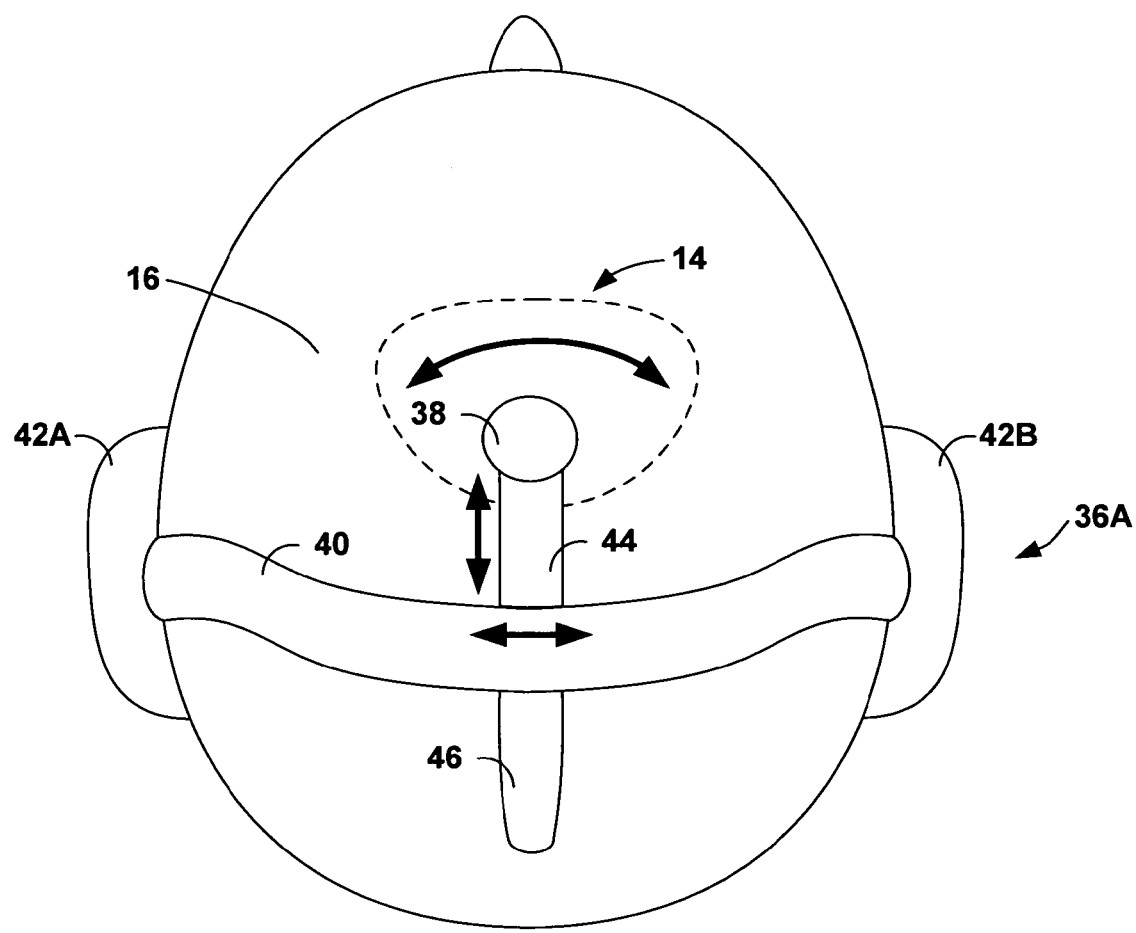
FIGS. 3A-3C are top-view diagrams illustrating exemplary headsets placed upon the head of the patient.

FIG. 3A is top-view diagram illustrating an exemplary headset 36A placed upon the head 16 of the patient 18. An energy delivery module 38, e.g., a primary coil, is adjustably coupled to headset 36A. In embodiments in which energy delivery module 38 comprises a primary coil, the coil may be surrounded by a housing formed of a material that permits induction, e.g., may be encapsulated in one or more of a silicone, polysulfone, polyvinylchloride, or the like. The primary coil may also act as a telemetry antenna for communication between recharge control unit 20 and IMD 14 or, in other embodiments, a separate telemetry antenna may be stacked on top of, or below the primary coil. As described above, patient 18 or a clinician may adjust the position of energy delivery module 38 to be located above and aligned with recharge module 30 of IMD 14.

In the illustrated embodiment, headset 36A includes a headset bar 40 that wraps around head 16 and supports both of earpieces 42A and 42B (collectively, "earpieces 42"), a coupling member 44, and a stabilizing member 46. The illustrated shapes, sizes, and positions of headset bar 40, earpieces 42, coupling member 44 and stabilizing member 46 are merely exemplary. Further, headsets according to the invention may include any number of, or may exclude, earpieces 42, coupling members 44 and stabilizing members 46.

Headset bar 40 may provide an inward pressure on earpieces 42 so as to secure headset 36A to head 16. Headset 36A may be adjusted to the size of head 16 by lengthening and shorting headset bar 40 to adjust the position of earpieces 42 in relation to the ears of the patient to ensure a proper fit, similar to conventional audio headsets known in the art. As shown in FIG. 3A, headset 36A only partially covers the head 16, and thus may be more comfortable for patient 18 to wear during recharging sessions.

Headset bar 40 and coupling member 44 may be hollow or otherwise formed to allow electrical conductors, e.g., cables, to be inserted within or routed along headset bar 40 and coupling member 44. For example, conductors carried by headset bar 40 and coupling member 44 may deliver AC voltages from cable 22 that is coupled to earpiece 42A to a primary coil included within energy delivery module 38. As another example, in some embodiments in which a telemetry antenna does not comprise a primary coil, a separate telemetry antenna may be carried by coupling member for location above IMD 14, e.g., within energy delivery module 38. In such embodiments, conductors carried by headset bar 40 and coupling member 44 may electrically couple the telemetry antenna to a telemety circuit within recharge control unit 20. In other embodiments, headset bar 40, as mentioned above, may further house at least some of the components of recharge control unit 20 in the form of flex tape circuits, capacitors and other such electrical circuits and components in order to improve the weight distribution of headset 36A.

Earpieces 42 may each comprise a speaker (not shown) to allow patient 18 to listen to audio provided by recharge control unit 20. Earpieces 42, while shown in FIG. 3A as completely covering the ears of patient 18, may not completely cover the ears or may include holes to allow patient 18 to hear ambient sound normally without restriction by earpieces 42. As described below, earpieces 42 may house at least some of the components of recharge control unit 20. While shown in FIG. 3A to include earpieces 42, headset 36A may not include earpieces 42 and may rely on the inward pressure provided by headset bar 40 to secure headset 36A to head 16. In other embodiments, headset 36A may include behind the ear members and other such earpiece replacements to secure headset 36A to head 16.

In the illustrated embodiment, coupling member 44 carries energy delivery module 38, and may be adjustably coupled to headset bar 40 by a fixation mechanism (not shown), such as a bolt and nut mechanism. In other words, coupling member 44 adjustably couples energy delivery module 38 to headset bar 40. Coupling member 44 may be moved laterally, anteriorly, and posteriorly, as shown by the horizontal and vertical arrows, respectively. Moreover, in some embodiments, coupling member 44 may pivot about its point of attachment with headset bar 40, as shown by the semi-circular arrow. Coupling member 44 may also be formed of a material that is semi-flexible or malleable, e.g., when heated, to enable a physician to mold coupling member 44 to fit the curvature of head 16. Alternatively, coupling member 44 may include a piece of malleable metal cased in a plastic that enables coupling member 44 to be molded. In this instance, the piece of metal may not extend the entire length of coupling member 44 so as not to interfere with the transmissions of energy delivery module 38.

Through movement of coupling member 44, patient 18 or a clinician may, for example, adjust the position of energy delivery module 38 along at least two axes, along three axes including a rotational axis, or four axes including the vertical axis in embodiments in which coupling member 44 may be molded. Coupling member 44 may be adjusted to allow energy delivery module 38 to be placed over and aligned with a recharge module 30 of an IMD 14 located at any of a variety of locations on or within the cranium of patient 18. In this manner, headset 36A may recharge an IMD, such as IMD 14, implanted in a variety of implant locations, as well as allow placement of energy delivery module 38 to account for anatomical differences between patients. For example, coupling member 44 may be adjusted to allow placement of energy delivery module over a an IMD 14 implanted on the crown of cranium 23 of patient 18, in the manner illustrated in FIG. 2, or, for example, on the occipital or temporal regions of cranium 23.

Stabilizing member 46 stabilizes headset 36A on head 16 of patient 18. Stabilizing member 46 extends down the back of cranium 16 and aids patient 18 in properly placing headset 36A on head 16, e.g., enables headset 36A to be placed at a consistent position on head 16, and may prevent movement of headset 36A on head 16 during recharging sessions. In this manner, stabilizing member 46 may facilitate consistent alignment of energy delivery module 38 with recharge module 30 of IMD 14.

Stabilizing member 46 may be formed of a material that is semi-flexible or malleable, e.g., when heated, to enable a physician to mold stabilizing member 46 to fit the curvature of head 16. Like coupling member 44, stabilizing member 46 may include a piece of malleable metal cased in a plastic that enables stabilizing member 46 to be molded. Alternatively, a number of stabilizing members formed of rigid materials may be preformed, and a clinician may select a stabilizing member that most closely matches the form of head 16. Stabilizing member 46 may be permanently affixed to headset bar 40, e.g., may be a protrusion that extends from headset bar 40, or may be coupled to headset bar as required by a clinician using a fixation mechanism similar to that used to couple coupling member 44 to headset bar 40. While shown affixed posteriorly, stabilizing member 46 may be affixed anteriorly and may further be of any size or shape. Stabilizing member 46 may be adjusted and fixed, and/or molded, by a clinician during a fitting session.

Figure 3B:
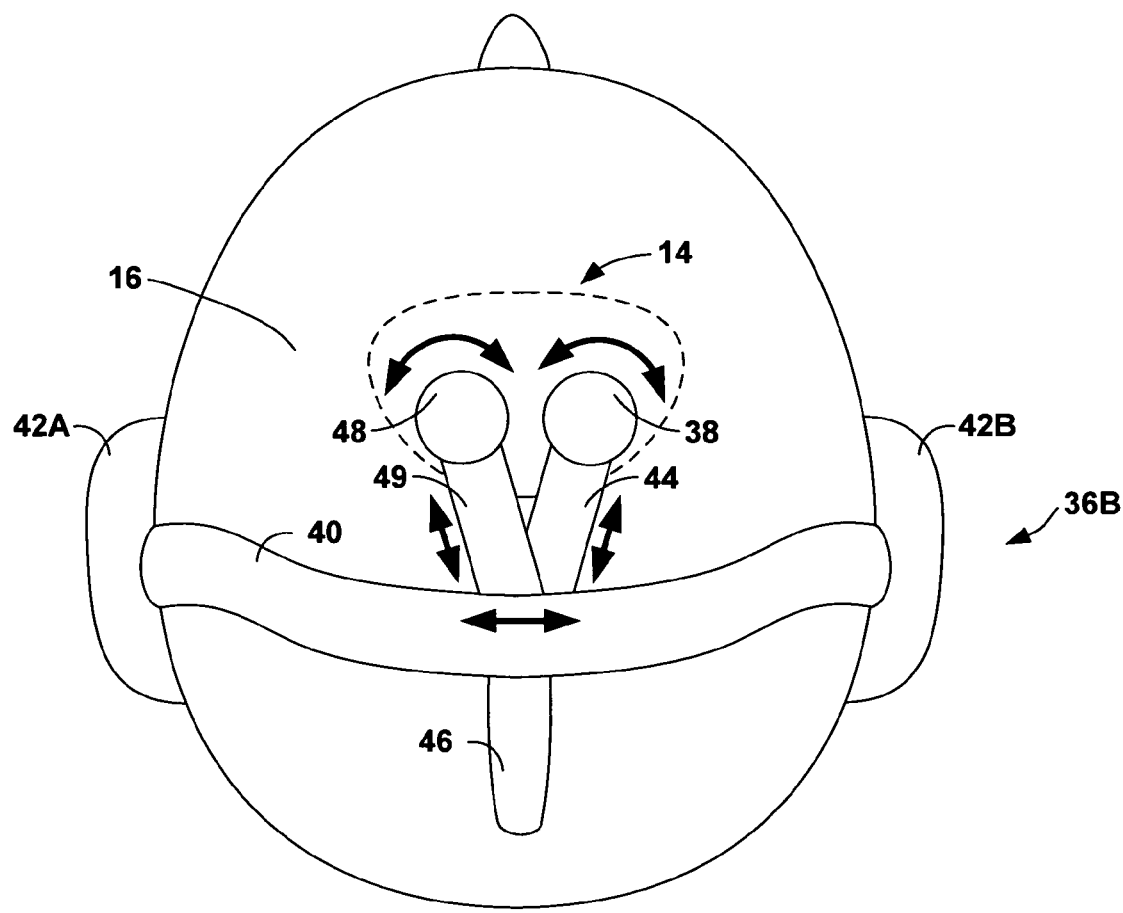

FIG. 3B is a top-view diagram illustrating another exemplary headset 36B placed upon head 16 of patient 18. Energy delivery module 38 is adjustably coupled to headset bar 40 by coupling member 44, as described above with reference to headset 36A and FIG. 3A. Additionally, in the illustrated embodiment, a telemetry antenna 48 is adjustably coupled to headset bar 40 by a second coupling member 49.

Coupling member 49 may be affixed to headset bar 40 via a fixation mechanism, such as a nut and bolt mechanism, which may be the same fixation mechanism used to couple coupling member 44 to headset bar 40, or a different fixation mechanism. Similar to coupling member, coupling member 49 may also be hollowed or otherwise configured to carry conductors that electrically couple telemetry antenna 48 to a telemetry circuit within recharge control unit 20, and may be malleable. Coupling member 49 may be adjusted by patient 18 or a clinician similarly to coupliug member so as to position telemetry antenna 48 above JMD 14 located anywhere on or within cranium 23 of patient. In this manner, headset 36B may possibly provide for more efficient data communications and energy delivery since telemetry antenna 48 and energy delivery module 38 may be more accurately positioned above IMD 14. For example, energy delivery module 38 may be positioned above and aligned with recharge module 30 of IMD 14, while telemetry antenna 48 is positioned above a telemetry antenna included within control module 34 of IMD 14. A headset 36B with energy delivery module 38 end telemetry coil 48 that are separately positionable may be particularly useful in conjunction with embodiments of IMD 14 in which recharge module 30 and control module 34 of IMD 14 are located a significant distance from each other, e.g., when recharge module 30 is located a significant distance from and "tethered" to other modules 32, 34 of IMD 14.

Figure 3C:
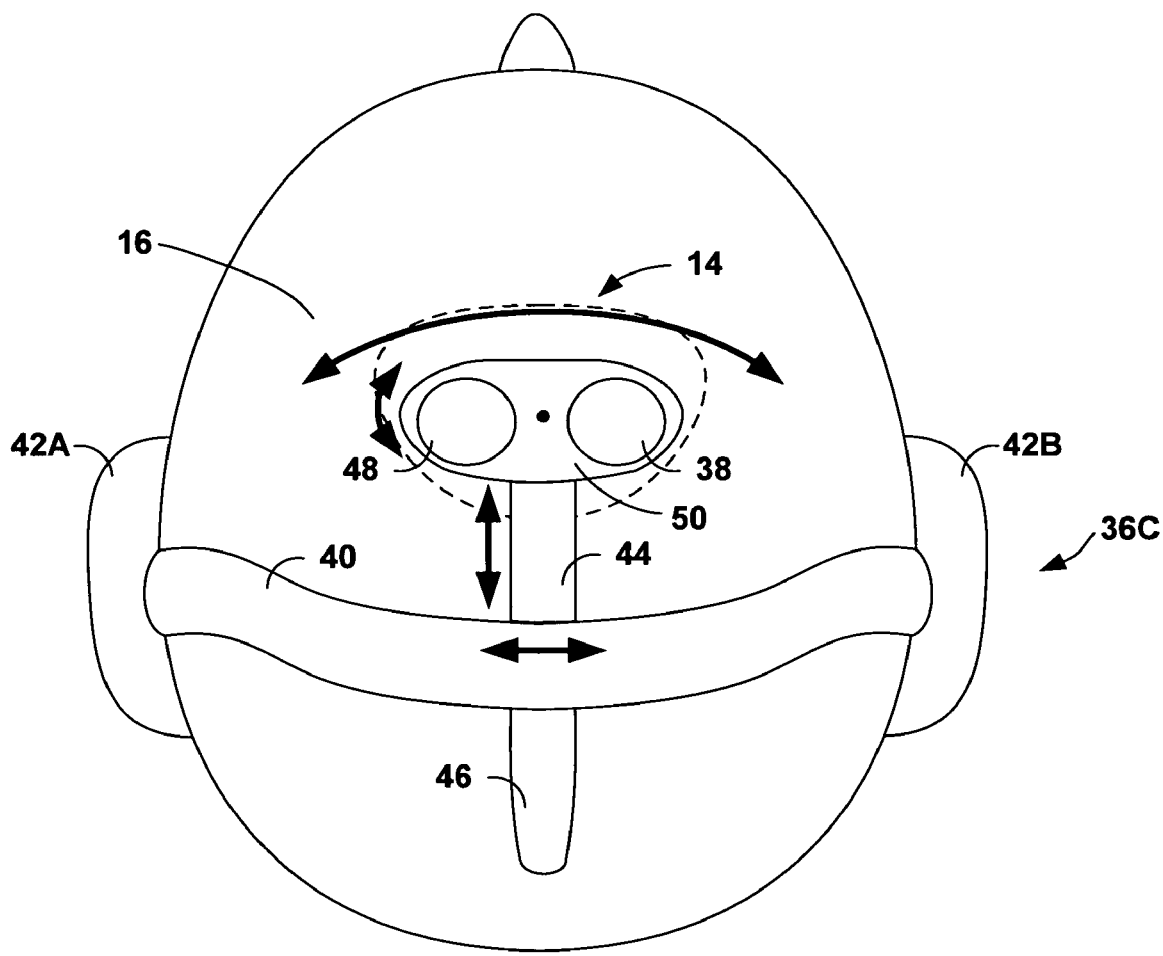

FIG. 3C is a top-view diagram illustrating yet another exemplary headset 36C placed upon head 16 of patient 18. Similar to headset 36B of FIG. 3B, headset 36C includes an energy delivery module 38 and separate telemetry antenna 48, however headset 36C includes only one coupling member 44. Energy delivery module 38 and telemetry antenna 48 may be encased in a common housing member 50, as shown in FIG. 3C.

Housing member 50 may, in some embodiments, be formed of a material that is semi-flexible or malleable, e.g., when heated, to enable a physician to mold housing member 50 to conform to the curvature of head 16. Housing member 50 couples to an end of coupling member 44 and may rotate about the point where housing member 50 couples to coupling member 44. Typically, housing member 50 is coupled to coupling member 44 as required by a clinician using a fixation mechanism similar to that used to couple coupling member 44 to headset bar 40. In some embodiments, housing member 50 is permanently affixed to coupling member 44, however this configuration may not allow housing member 50 to rotate about the point where housing member 50 couples to coupling member 44. Rotation and molding of housing member 50 may allow a user to place energy delivery module 38 and telemetry antenna 48 above and proximate to recharge module 30 and control module 34 of IMD 14, respectively.

Although described above as carried by one of coupling members 44, 49, in various embodiments a telemetry antenna 48 may be located anywhere on or within a headset 36. For example, in some embodiments, a telemetry antenna 48 may be located within one of earpieces 42 of a headset 36. In other embodiments, a telemetry antenna is not located on or with headset 36 at all, and may instead be located, for example, within recharge control unit 20.

Figure 4A:
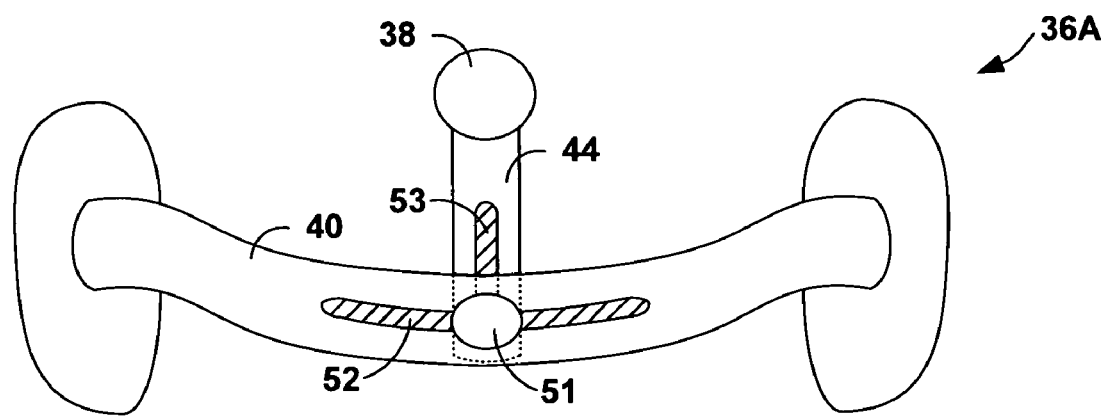
FIGS. 4A-4B are top-view and rear-view diagrams, respectively, further illustrating the exemplary headset of FIG. 3A.
Figure 4B:
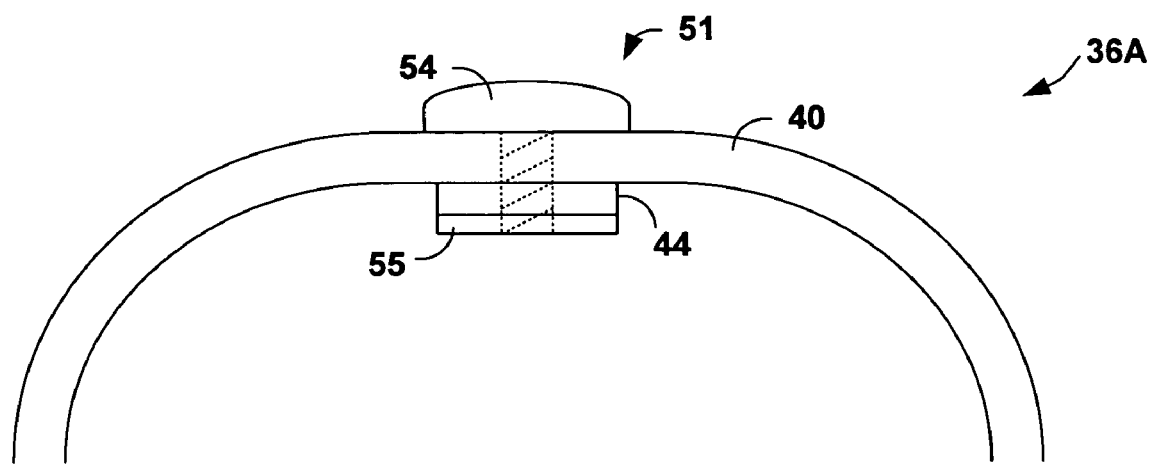

FIGS. 4A-4B are top-view and rear-view diagrams, respectively illustrating headset 36A of FIG. 3A in greater detail. In particular, FIG. 4A illustrates an example fixation mechanism 51 used to connect coupling member 44 to headset bar 40. Fixation mechanism 51 may be adjusted by patient 18 or a clinician between a first state in which coupling member 44 may be moved and a position of energy delivery module 38 may be adjusted, and a second state in which coupling member 44 and the position of energy delivery module 38 are substantially fixed. As illustrated in FIG. 4B, fixation mechanism 51 may include a threaded bolt-like member 54 and a nut-like member 55 that allow movement of coupling member 44 when loosened, and cooperate to substantially lock coupling member 44 in a desired position when tightened.

In the illustrated embodiment, the threaded portion of bolt-like member 54 extends through a hole 52 formed in headset bar 40. Hole 52, as shown in FIG. 4A, may comprise an oblong hole in headset bar 40 to facilitate lateral positioning of energy delivery module 38. Bolt-like member 54 also extends through an oblong hole 53 in recharge arm 44 to facilitate anterior-posterior positioning of energy delivery module 38. Coupling member 44 may also rotate about fixation mechanism 51 for rotational positioning of energy delivery module. In some embodiments, fixation mechanisms similar to that illustrated in FIGS. 4A and 4B, or the same fixation mechanism 51, may also be used to allow adjustment and fixation of a stabilizing member 46 or an additional coupling member 49 that carries a telemetry antenna 48 within holes 52, 53. The size and shapes of holes 52, 53 are merely exemplary.

Further, the type of fixation mechanism 51 illustrated in FIGS. 4A-4B is merely exemplary. A recharging headset according to the invention may include any type of fixation mechanism. For example, the position of coupling member 44 may be fixed by a friction mechanism until coupling member is forcibly moved to another position.

Other fixation mechanisms may include glue or set screws to permanently fix coupling member 44. In some embodiments, fixation mechanisms may include features, such as detents, included within oblong hole 53, and corresponding features included on coupling member 44. The features may interact to fix the position of coupling member 44 and energy delivery module 38. In such embodiments, the fixation mechanism may further include a mechanism, such as a lever lock, to position the one or more features associated with coupling member 44 out of the path of features included in oblong hole 53, thereby allowing coupling member 44 to be positioned without obstruction. The mechanism can then reposition the features associated with coupling member 44 back in the path of the features included in oblong hole 53 when coupling member 44 is properly positioned to prevent further movement of coupling member 44.

Figure 5:
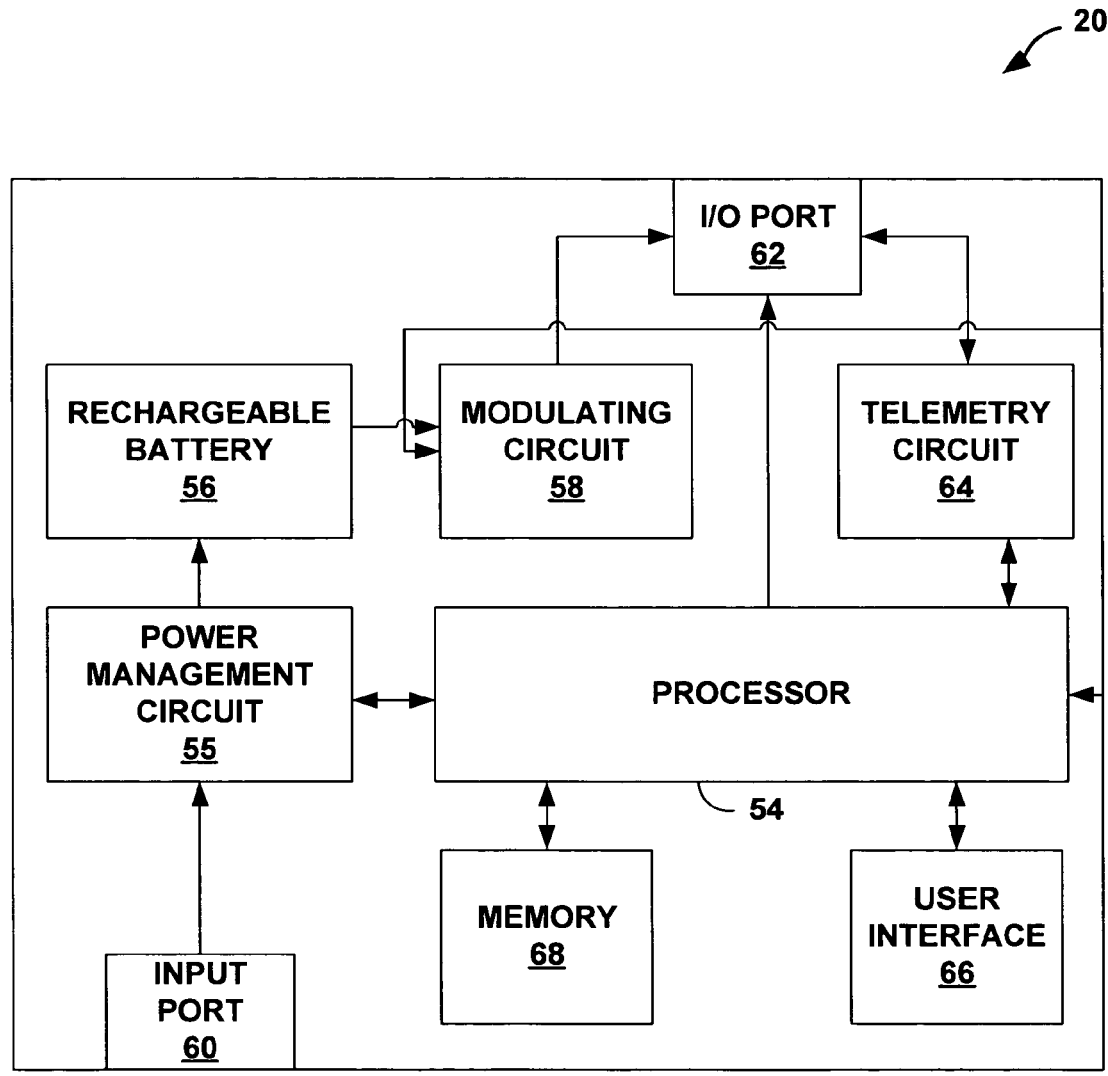
FIG. 5 is a functional block diagram illustrating the recharge control unit of FIG. 1.

FIG. 5 is a block diagram illustrating recharge control unit 20 of FIG. 1 in greater detail. Recharge control unit 20, and more particularly a processor 54 of recharge control unit 20, controls delivery of energy from a rechargeable battery 56 to the power source of IMD 14 via an energy delivery module 12, 38. Processor 54 may take the form of a microprocessor, digital signal processor (DSP), application specific integrated circuit (ASIC), field-programmable gate array (FPGA), or other logic circuitry. Rechargeable battery 56 may be any conventional rechargeable battery, such as a Lithium-Ion rechargeable battery, Nickel-Metal Hydride rechargeable battery, or a Nickel-Cadmium rechargeable battery.

Recharge control unit 20 further includes a power management circuit 55 and a modulating circuit 58. Power management circuit 55 recharges rechargeable battery 56 using an AC voltage received from an input port 60, which is coupled to an external power supply. Input port may be coupled to the power supply by placing recharge control unit 20 into a cradle that is plugged into a wall receptacle, or by plugging recharge control unit 20 directly into a wall receptacle. Power management circuit 55 or the cradle may include a step down transformer and a rectifier to convert the AC voltage into a DC voltage usable for recharging rechargeable battery 56. Rechargeable battery 56 may be recharged in between recharge sessions in which the power source of IMD 14 is recharged, e.g., recharge control unit may be left in the cradle or plugged into the wall for recharging between recharging sessions. Rechargeable battery 56 is merely an example of a power source and recharge control unit 20 may include other forms of power such as non-rechargeable batteries, fuel cells, capacitors, super capacitors, solar cells, nuclear cells, or any combination thereof.

Modulating circuit 58 converts a DC voltage provided by battery 56 into an AC voltage at a desired amplitude and frequency for delivery to energy delivery module 12, 38.

Conductors within cable 22 may be coupled to modulating circuit 58 via an I/O port 62 to receive the AC voltage output by modulating circuit 58. Processor 54 controls the recharging of rechargeable battery 56 and delivery of power from battery 56 to energy delivery module 12, 38 by providing control signals to power management circuit 55 and modulating circuit 58. In some embodiments, recharge control unit 20 does not include rechargeable battery 56, but instead includes transformer and modulator circuitry to convert an AC voltage received from a wall receptacle via input port 60 to an AC voltage with suitable amplitude and frequency for recharging of IMD 14.

In some embodiments, recharge control unit 20 includes telemetry circuit 64 that allows processor 54 to communicate with IMD 14. Telemetry circuit 66 converts analog telemetry signals received from IMD 14 via a primary coil of energy delivery module 38 or a dedicated telemetry antenna 48, depending on the embodiment, into digital signals for processing by processor 54. Telemetry circuit 66 may also convert digital signals from processor 54 into analog signals for transmission to IMD 14. Cable 22 may comprise conductive elements that couple the primary coil or antenna 48 to telemetry circuit 64 via I/O port 62 when cable 22 is inserted into I/O port 62. In some embodiments, antenna 48 is not located on or within headset 36 as described above, and cable 22 need not carry conductors to couple antenna 48 to telemetry circuit 64.

Processor 54 may, for example, receive recharge status information from IMD 14 during a recharging session via telemetry circuit 64. Recharge status information may include periodic indications of the extent to which the power source of IMD 14 is currently recharged, periodic indications of the time remaining to fully recharge the power source, or an indication that the power source is fully recharged. Processor 54 may control or terminate delivery of energy by modulating circuit 58 based on one or more of these indications. In some embodiments, processor 54 periodically receives voltages and/or temperatures from IMD 14, and determines the extent to which the power source of IMD 14 is currently recharged, the time remaining to fully recharge the power source, or whether the power source is fully recharged based on the voltages and/or temperatures Processor 54 may present such recharge status information to patient 18 via a user interface 66. User interface 66 may include, for example, a display and one or more speakers. The speakers may be included within a housing of recharge control unit 20, or within earpieces 42 of headset 10, 36 and coupled to processor 54 by cable 22 and I/O port 62. For example, processor 54 may present textual or graphical indications of the extent to which the power source of IMD 14 is currently recharged and/or the time remaining to fully recharge the power source via the display. As another example, processor 54 may present an audible indication when the power source of IMD 14 is fully recharged via the speakers. In some embodiments, user interface 66 includes input media, such as a touch screen, buttons, keypads, pointing device, or the like. In such embodiments, patient 18 may control recharging, e.g. may initiate or terminate recharging, via user interface 66.

During alignment of energy delivery module 12, 38 with a recharge module 30 of IMD 14, e.g., during a headset fitting session, processor 54 may receive alignment information. The alignment information may include an indication of when energy delivery module 12, 38 is properly aligned with recharge module 30, or of the relative degree to which energy delivery module 12, 38 is properly aligned a recharge module 30. The alignment information may include a measure of the impedance, current or other properties at energy deliver module 12, 38. In some embodiments, IMD 14 communicates alignment information to processor 54 via telemetry antenna 48, I/O port 62, and telemetry circuit 64. In these embodiments, sensors within IMD 14 may measure one or more properties of the power source of IMD 14, such as current, temperature, or both, or one or more properties of the recharge module 30 of IMD 14, such as impedance, current or other properties, and IMD 14 communicates this alignment information to processor 54 via telemetry antenna 48. In other embodiments, processor 54 receives both alignment information gathered from energy delivery module 12, 38 and alignment information communicated via telemetry antenna 48 and processes both to generate a coupling resonant frequency, a coupling phase or other alignment information. Processor 54 may present the alignment information to the aligning user, e.g., patient 18 or the clinician, via user interface 56, such an audible indication when the modules are aligned via one or more speakers, or a graphical representation of the relative alignment of the modules via a display.

In some embodiments, recharge control unit 20 includes a memory 68. Processor 54 may store data received from telemetry circuit 64 in memory 68. Memory 68 may also store program instructions that, when executed by processor 54, cause processor 54 and recharge control unit 20 to perform the functions ascribed to them herein. Memory 68 may include any removable or non-removable magnetic, optical, or electrical media, such as one or more of a random access memory (RAM), read-only memory (ROM), CD-ROM, magnetic disk, memory stick, electronically-erasable programmable ROM (EEPROM), flash memory, or the like.

In some of these embodiments, processor 54 may be capable of playing media to, for example, entertain patient 18 during recharging sessions. For example, processor 54 may include an audio module, such as an MP3 module, and memory 68 may further store audio files, such as MP3 files, that encode audio content. The audio module may play the audio files stored in memory 68 and transmit the audio content resulting from playing the audio files to I/O port 62. Patient 18 listens to the audio content via one or more speakers included within earpieces 42. Patient may interact with processor 54 via user interface 66 to select files for playback from among those stored in memory 68. In other embodiments, recharge control unit 20 may include a radio, or a network interface to allow patient 18 to access the Internet via recharge control unit 20. Processor 54 may further execute programs, such as games, stored in memory 68 that may entertain or occupy patient 18.

To use a recharging system 2 to recharge a power source of an IMD 14 during a recharging system, patient 18 places headset 10 upon head 16 so as to bring energy delivery module 12, 38 proximal to IMD 14, and interacts with recharge control unit 20 via user interface 66 to initiate charging. Upon receiving the request to begin charging from user interface 66, processor 54 causes modulating circuit 58 to begin converting the DC voltage stored within rechargeable battery 56 to an AC voltage and transferring the AC voltage to I/O port 62. The AC voltage travels along cable 22 into energy delivery module 12, 38. In embodiments in which energy delivery module 12, 38 comprises a primary coil, the AC voltage presented to the primary coil induces an AC voltage within a secondary coil of recharge module 30 of IMD 14, which is used by IMD 14 to recharge the power source of IMD 14, as described above.

While charging occurs, processor 54 may poll IMD 14 via telemetry circuit 66 and either the primary coil or a dedicated telemetry antenna 48 to determine the status of the rechargeable battery within IMD 14. Processor 54 may present information pertinent to the status of the rechargeable battery within IMD 14 to patient 18 via a display of user interface 64. Once processor 54 determines charging is complete, processor 54 may cause user interface 64 to signal patient 18 that charging is complete. User interface 64 may present a message indicating successful charging of the battery within IMD 14 via a display, issue a tone or beep, vibrate, or perform other such actions to signal successful charging.

Figure 6:
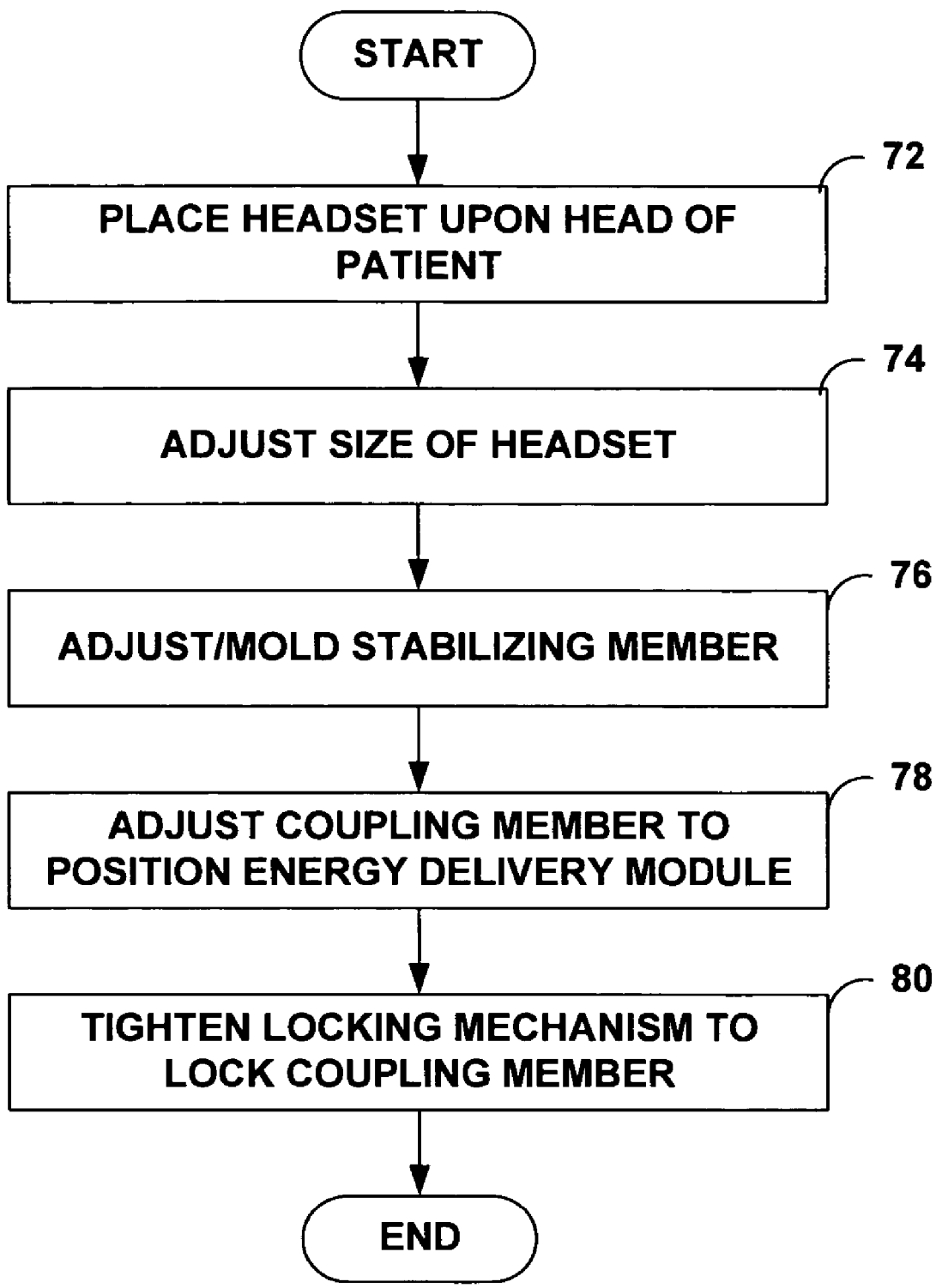
FIG. 6 is a flow diagram illustrating an exemplary process by which a clinician fits a headset of a recharging system to a patient.

FIG. 6 is a flow diagram illustrating an exemplary process by which a user fits a headset, such as headset 36, to a patient, such as patient 18. The exemplary process illustrated in FIG. 6 may be performed by patient 18 prior to a recharging session, but is preferably performed a single time by a clinician during a headset fitting session at a clinic. Initially, the clinician places headset 36A (FIG. 3A) upon the head 16 of patient 18 (72), and adjusts the size of headset bar 40 to the size of the head 16 (74). Headset 36A, as shown in FIG. 3, only partially covers head 16 providing more comfort to patient 18 with respect to conventional recharge mechanisms while also providing adjustability to facilitate efficient recharging of an IMD, such as IMD 14, implanted on or within the cranium of patient 18.

In some embodiments, the clinician may determine that patient 18 requires a stabilizing member 46 to maintain headset 36 at a desired position on head 16. The clinician determines whether to include a stabilizing member by, for example, monitoring patient 18 when placing headset 36A upon head 16. If the patient experiences difficulty correctly placing headset 36A in a consistent position on head 16, or headset 36A moves on head 16, the clinician may attach stabilizing member 46 to headset 36A with a fixation mechanism. The clinician may then adjust the position of the stabilizing member 46 and/or mold the stabilizing member 46 to fit the curvature of head 16 (76). In some embodiments, the clinician may not need to form stabilizing member 46, and instead the clinician selects a stabilizing member from a plurality of options that most closely fits head 16, as described above. Further, in some embodiments, stabilizing member 46 is not a separate member from headset bar 40, but is instead an integral protrusion from headset bar 40.

The clinician positions energy delivery module 38 above a recharge module 30 of IMD 14 by adjusting coupling member 44 of headset 36A (78). As described above, coupling member 44 may be moved laterally and in a posterior-anterior direction with respect to patient 18. The clinician may further adjust coupling member 44 by pivoting coupling member 44 about a point of contact with headset bar 40 and molding coupling member 44. In some embodiments, as described above, the clinician may further rotate and mold a housing member that is carries energy delivery module 38 and is coupled to coupling member 44. Upon positioning energy delivery module 38, the clinician adjusts a fixation mechanism 51, such as bolt-like member 53 and nut-like member 54, to substantially lock the position of coupling member 44 (80) and thus the position of energy delivery module 38 with respect to the recharge module 30. In some embodiments, as described above, the clinician may receive alignment information via a user interface 66 of recharge control unit 20, and may use the alignment information to determine when energy delivery module 38 is properly aligned with the recharge module 30 of IMD 14.

While fitting a headset is explained in the context of headset 36A, the clinician may also fit a headset similar to headset 36B of FIG. 3B. The process of fitting headset 36B is similar to fitting headset 36A, however headset 36B requires an additional step to position a coupling member 49 that carries a telemetry antenna 48 proximal to IMD 14.

Figure 7:
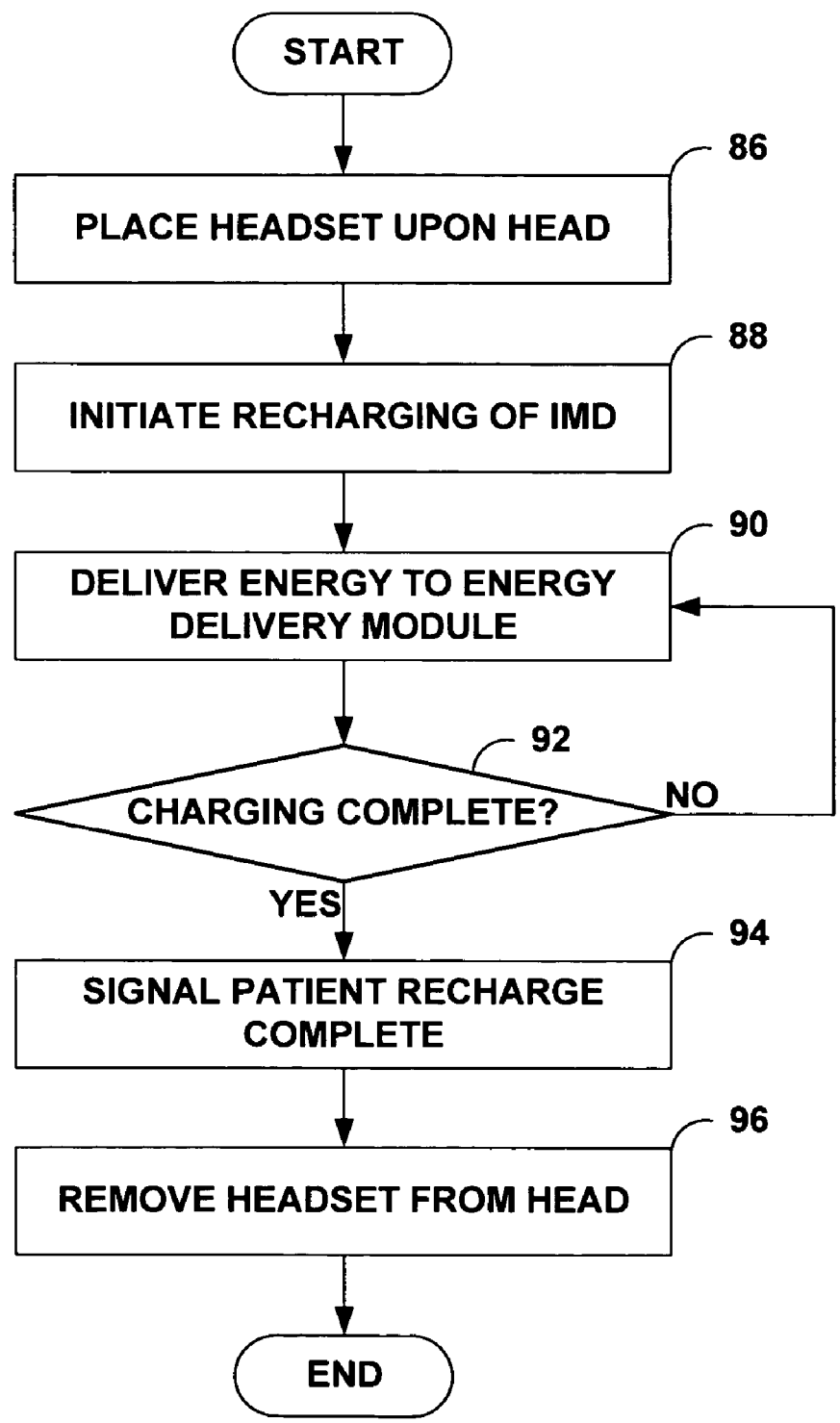
FIG. 7 is a flow diagram illustrating an exemplary process for recharging an IMD implanted upon the cranium of a patient.

FIG. 7 is a flow diagram illustrating an exemplary process by which patient 18 places a headset 36A (FIG. 3A), upon his or her head 16 to recharge IMD 14. Patient 18 begins by placing headset 36A upon his or her head 16 (86) and initiating the recharge of IMD 14 (88) via user interface 66 (FIG. 5) of recharge control unit 20. Typically, patient 18 initiates the recharge by selecting recharge options presented by user interface 66, however recharge control unit 20 may automatically begin recharging after a pre-set time limit is exceeded.

Once the recharge is initiated via user interface 66, processor 54 causes modulating circuit 58 to begin converting the DC voltage stored in rechargeable battery 56 into an AC voltage. Modulating circuit 58 delivers the AC voltage to headset 36A, and more particularly, to energy delivery module 38 via I/O port 60 and cable 22 (90). The AC voltage may, for example, be presented to a primary coil of energy delivery module 38, and may induce an AC voltage within a secondary coil associated with IMD 14, as described above.

In further embodiments, recharge control unit 20 may communicate with IMD 14 via a primary coil within energy delivery module 38, or via a separate telemetry antenna 48. Recharge control unit 20 includes telemetry circuit 66 to enable communication with IMD 14, as described above. Via communications with IMD 14, recharge control unit 14 may receive recharge status information, e.g., determine whether charging of IMD 14 is complete (92). In embodiments that do not include telemetry circuit 66, processor 54 may determine charging is complete after a pre-set interval of time has expired. In the event charging is not complete, processor 54 continues to control delivery of energy from rechargeable battery 56 to energy delivery module 38 (90).

However, in the event the charging of IMD 14 is determined to be complete, processor 54 terminates delivery of energy to energy delivery module 38, and causes user interface 64 to issue a signal to patient 18 by way of one of the signaling mechanism described above that indicates to patient 18 that charging is complete (94). In response to the signal, patient 18 may remove headset 36A from his or her head 16 (96).

While discussed in the context of a separate headset 36A and recharge control unit 20, headset 36A may integrate the components, such as processor 54, of recharge control unit 20 into earpieces 42 of headset 36A, 36B. As described below, a headset incorporating the components of recharge control unit 20 may offer a less cumbersome recharge device by eliminating the need for cable 22.

Figure 8:
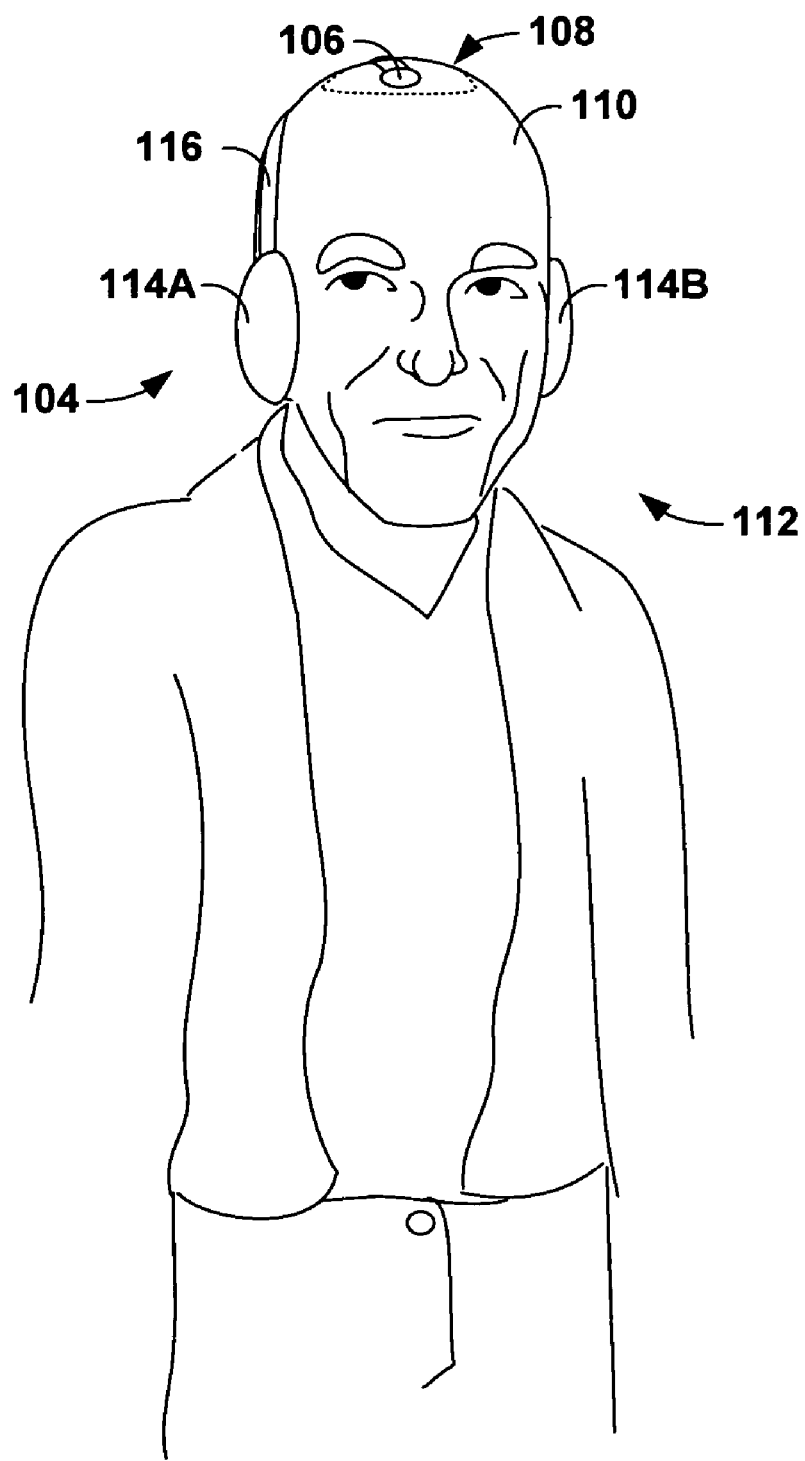
FIG. 8 is a conceptual diagram illustrating another example recharging system that recharges a power source of an implantable medical device (IMD) implanted on the cranium of a patient.

FIG. 8 is a conceptual diagram illustrating another example headset 104 that positions an energy delivery module 106 proximal to an implantable medical device (IMD) 108 implanted on the cranium 110 of a patient 112. In the illustrated embodiment, headset 104 incorporates the components of recharge control unit 20 (FIG. 5) into earpieces 114A and 114B. The components, such as processor 54, power management circuit 55, rechargeable battery 56, and the like, may be distributed between earpieces 114A and 114B (collectively, "earpieces 114") to provide adequate balance and comfort when worn by patient 112. For example, right earpiece 114A may include processor 54, power management circuit 55, and telemetry circuit 66, while left earpiece 114B includes rechargeable battery 56, modulating circuit 58 and user interface 64. Headset bar 116 may be hollowed or otherwise configured to conductors that electrically couple the various components distributed between earpieces 114. In all other aspects, headset 104 performs in a manner substantially similar to headset 36A.

Figure 9:
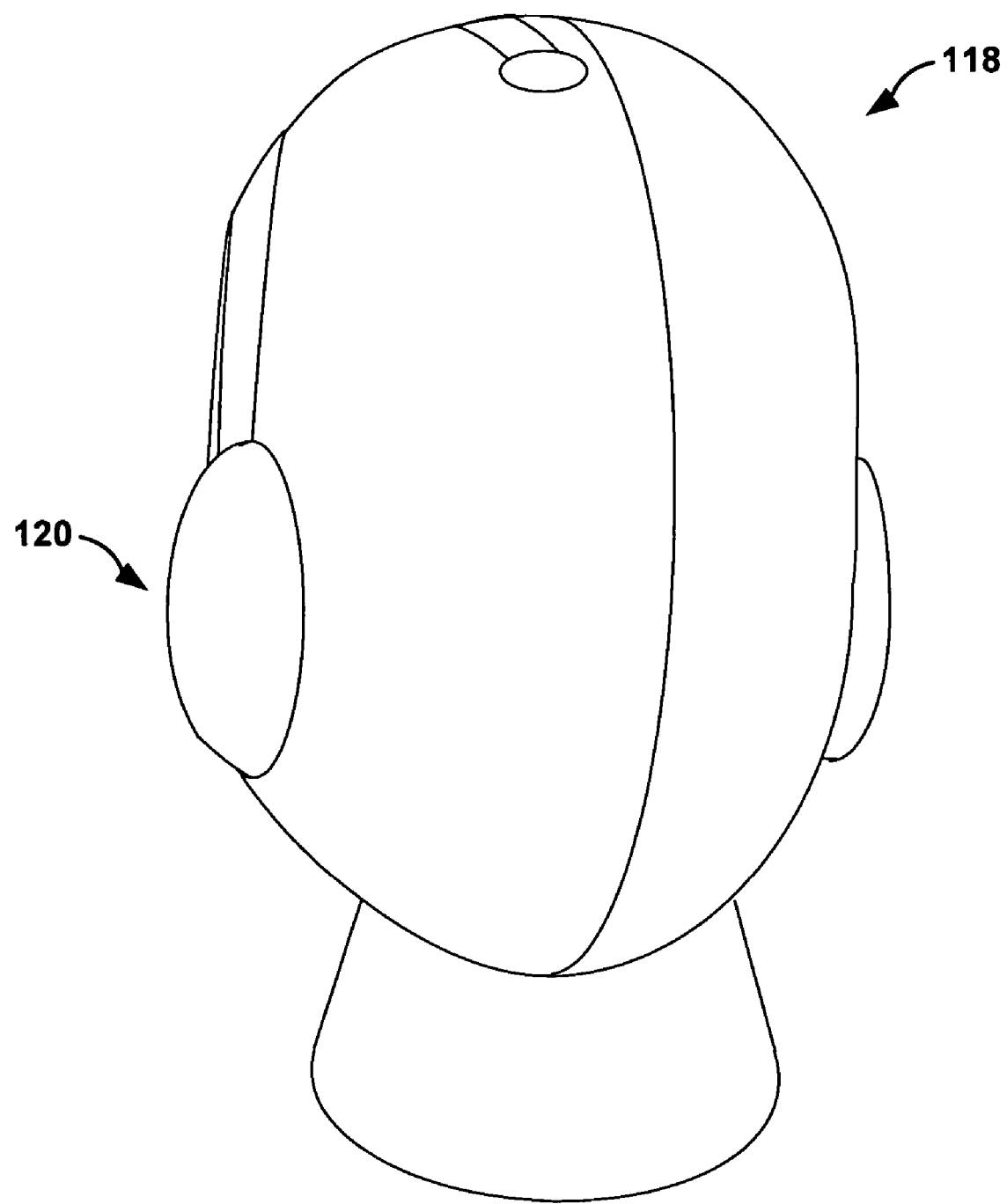
FIG. 9 is a conceptual diagram illustrating a recharge cradle shaped in the form of a head to recharge a rechargeable battery of the headset of FIG. 8.

FIG. 9 is a conceptual diagram illustrating a recharge cradle 118 shaped in the form of a head to recharge a rechargeable battery, such as rechargeable battery 56 (FIG. 5), of headset 120. Headset 120 may include contacts (not shown) or some other means for electrically coupling headset 120 to recharge cradle 118. The contacts may be included on the earpieces of headset 120 and may come into contact with similar contacts (not shown) included within recharge cradle 118. Once the contacts of recharge cradle 118 and headset 120 come into contact, recharge cradle 118 may recharge headset 120. Recharge cradle 118 may plug into a transformer that is plugged directly into the wall and include electronic components, such as a rectifier, to charge headset 120. Recharge cradle 118 may also serve as a suitable location for storing headset 120 even when recharging is not required.

Various embodiments of the invention have been described. However, one skilled in the art will appreciate that various modifications may be made to the described embodiments without departing from the scope of the invention. For example, although described herein primarily in the context of transcutaneous inductive energy transfer, other techniques for transcutaneous energy transfer may be used. In some embodiments, for example, an energy delivery module of a headset and a recharge module of an IMD may comprise ultrasonic transducers, such as piezoelectric crystals, and energy may be transferred from the energy delivery module to the recharge unit in the form of ultrasonic waves. In other embodiments, an energy delivery module of a headset and a recharge module of an IMD may comprise a light source and a photoreceptor respectively, and energy may be transferred form the energy delivery module to the recharge unit in the form of light waves. In other words, in various embodiments, the energy delivery module of a headset and the recharge module of an IMD may take the form of any type of transducers, and any form of energy may be transcutaneously transferred between them.

Further, although described herein primarily in the context of recharging a rechargeable battery of a neurostimulator implanted on the crown of the cranium of the patient, the invention is not so limited. A recharging system according to the invention may be used to recharge any type of power source of any type of implantable medical device. Further, a recharging system according to the invention may be configured or adjusted to recharge an IMD located anywhere on or within the cranium of the patient, such as the illustrated IMD implanted on the crown of the cranium, or an IMD implanted on or under an occipital or temporal region of the cranium. These and other embodiments are within the scope of the following claims.

The invention claimed is:

1. A recharging system comprising:
 a headset that is configured for placement over a head of a patient, wherein the headset extends from a first end to a second end;
 an energy delivery module adapted to deliver recharge energy to a rechargeable power source of a medical device that is implanted at least one of on or within a cranium and under a scalp of the patient; and
 a coupling member to couple the energy delivery module to a medial portion of the headset between the first and second ends of the headset, wherein the coupling member is adjustably coupled to the headset such that a position of the coupling member is adjustable along at least two axes of motion.

2. The recharging system of claim 1, wherein the energy delivery module comprises a primary coil that delivers energy to the power source of the medical device via transcutaneous inductive energy transfer to a secondary coil associated with the medical device.

3. The recharging system of claim 1, wherein the coupling member is adjustably coupled to the headset such that the position of the coupling member is adjustable along at least three axes of motion, and one of the axes of motion comprises a rotational axis.

4. The recharging system of claim 1, wherein the coupling member is moldable.

5. The recharging system of claim 1, further comprising a fixation mechanism that couples the coupling member to the headset, wherein the fixation mechanism is manipulatable between a first state in which the position of the coupling member is adjustable and a second state in which the position of the coupling member is substantially fixed.

6. The recharging system of claim 1, wherein the headset partially covers a top of the head.

7. The recharging system of claim 1, further comprising a recharge control unit that controls delivery of energy to the power source of the medical device.

8. The recharging system of claim 7,
 wherein the power source of the medical device is a first power source, and
 wherein the recharge control unit comprises a second power source, and controls delivery of energy from the second power source to the first power source.

9. The recharging system of claim 7, further comprising a telemetry antenna, wherein the recharge control unit further comprises a telemetry circuit electrically coupled to the telemetry antenna, and the recharge control unit communicates with the medical device via the telemetry circuit and the telemetry antenna.

10. The recharging system of claim 9, wherein the energy delivery module comprises a coil that delivers energy to the power source of the medical device, and the telemetry antenna comprises the coil.

11. The recharging system of claim 9, wherein the coupling member couples the energy delivery module and the telemetry antenna to the headset.

12. The recharging system of claim 11, further comprising a housing member that is coupled to the coupling member and houses the energy delivery module and the telemetry antenna.

13. The recharging system of claim 12, wherein the housing member is adjustably coupled to the coupling member.

14. The recharging system of claim 12, wherein the housing member is moldable.

15. The recharging system of claim 9, wherein the coupling member comprises a first coupling member, the system further comprising
 a second coupling member that couples the telemetry antenna to the headset, wherein the second coupling member is adjustably coupled to the headset.

16. The recharging system of claim 9, wherein the recharge control unit receives recharge status information from the medical device via the telemetry antenna and the telemetry circuit.

17. The recharging system of claim 7, wherein the recharge control unit includes a user interface, and presents information to the patient via the user interface.

18. The recharging system of claim 17, wherein the recharge control unit presents alignment information to the patient via the user interface.

19. The recharging system of claim 17, wherein the recharge control unit presents recharge status information to the patient via the user interface.

20. The recharging system of claim 17, wherein the user interface comprises a display, and the recharge control unit presents information to the patient via the display.

21. The recharging system of claim 17, wherein the headset comprises at least one earpiece that includes a speaker, the user interface comprises the speaker, and the recharge control unit presents information to the patient via the speaker.

22. The recharging system of claim 7, wherein the recharge unit comprises a user interface, and at least one of initiates delivery of energy and terminates delivery of energy based on a command received from the patient via the user interface.

23. The recharging system of claim 7, wherein the recharge control unit is housed separately from the headset and is electrically coupled to at least one of the headset and the energy delivery module by a conductor.

24. The recharging system of claim 23, wherein the recharge control unit is configured to be worn by the patient.

25. The recharging system of claim 7, wherein the recharge control unit is integrated with the headset.

26. The recharging system of claim 25, wherein the headset comprises at least one earpiece, and the recharge control unit is housed by the at least one earpiece.

27. The recharging system of claim 1, further comprising a stabilizing member that extends from the headset to stabilize a position of headset relative to the head.

28. The recharging system of claim 27, wherein the stabilizing member substantially conforms to a curvature of the head of the patient.

29. The recharging system of claim 27, wherein the stabilizing member is moldable.

30. The recharging system of claim 1, wherein the power source of the medical device comprises a rechargeable battery.

31. The recharging system of claim 1, wherein the medical device is coupled to a lead that is implanted at least one of within or adjacent to a brain of the patient, and the medical device at least one of delivers stimulation to the brain or monitors electrical activity within the brain via the lead.

* * * * *